(12) United States Patent
Chauhan et al.

(10) Patent No.: US 10,362,956 B2
(45) Date of Patent: Jul. 30, 2019

(54) SYSTEM AND METHOD FOR ROTOR DETECTION IN CARDIAC FIBRILLATION

(71) Applicant: University Health Network, Toronto (CA)

(72) Inventors: Vijay Singh Chauhan, Toronto (CA); Rupin Haily Dalvi, Toronto (CA)

(*) Notice: Subject to any disclaimer, the term of this patent is extended or adjusted under 35 U.S.C. 154(b) by 0 days.

(21) Appl. No.: 15/677,711

(22) Filed: Aug. 15, 2017

(65) Prior Publication Data
US 2018/0042503 A1     Feb. 15, 2018

Related U.S. Application Data

(60) Provisional application No. 62/374,997, filed on Aug. 15, 2016.

(51) Int. Cl.
| | | |
|---|---|---|
| *A61B 5/04* | (2006.01) | |
| *A61B 5/046* | (2006.01) | |
| *A61B 18/14* | (2006.01) | |
| *A61B 5/00* | (2006.01) | |

(Continued)

(52) U.S. Cl.
CPC .......... *A61B 5/046* (2013.01); *A61B 5/04012* (2013.01); *A61B 5/4836* (2013.01); *A61B 18/00* (2013.01); *A61B 18/1492* (2013.01); *A61B 5/0422* (2013.01); *A61B 5/7253* (2013.01); *A61B 5/7264* (2013.01); *A61B 2018/00351* (2013.01); *A61B 2018/00434* (2013.01); *A61B 2018/00577* (2013.01); *A61B 2018/00839* (2013.01)

(58) Field of Classification Search
CPC . A61B 5/04012; A61B 5/046; A61B 18/1492; A61B 2018/00577
See application file for complete search history.

(56) References Cited

U.S. PATENT DOCUMENTS

| | | | |
|---|---|---|---|
| 9,433,365 B1* | 9/2016 | Lin | A61B 5/04012 |
| 2014/0088395 A1* | 3/2014 | Dubois | A61B 5/044 |
| | | | 600/382 |

(Continued)

OTHER PUBLICATIONS

Andrade, et al., "The clinical profile and pathophysiology of atrial fibrillation: relationships among clinical features, epidemiology, and mechanisms", Circ Res, 2014; 114(9):1453-68.

(Continued)

*Primary Examiner* — Joseph M Dietrich
(74) *Attorney, Agent, or Firm* — Bereskin & Parr LLP/S.E.N.C.R.L., s.r.l.; Tony Orsi

(57) ABSTRACT

Various embodiments are described herein for detecting a rotor at a location of a heart that experiences cardiac fibrillation. This generally involves obtaining a plurality of bipolar EGMs for a recording duration using a circular bipolar electrode array positioned at the location of the heart; detecting a dominant periodicity Cycle Length (CL) and identifying periodic activations for each bipolar EGM associated with the dominant periodicity CL; tracking the identified periodic activations across each bipolar EGM to define rotational activations and determining when a path taken by the tracked rotational activations corresponds to a rotational activation pattern of a rotor; and detecting the rotor when a number and completeness of the tracked rotational activations meet predefined rotor criteria.

29 Claims, 20 Drawing Sheets

(51) Int. Cl.
    A61B 18/00    (2006.01)
    A61B 5/042    (2006.01)

(56) References Cited

U.S. PATENT DOCUMENTS

2017/0079539 A1* 3/2017 Chauhan ............ A61B 5/04012
2017/0311835 A1* 11/2017 Narayan .............. A61B 5/0422

OTHER PUBLICATIONS

Benitez, et al., "The use of the Hilbert transform in ECG signal analysis", Computers in Biology and Medicine, 2001; 31(5): 399-406.
Coast, et al., "An approach to cardiac arrhythmia analysis using hidden Markov models", IEEE Trans Biomed Eng,, 1990; 37(9): 826-836.
Dalvi, et al., "Reviving the maximum likelihood method for detecting dominant periodicities from near-periodic signals," presented at the 2013 IEEE Digital Signal Processing and Signal Processing Education Meeting (DSP/SPE), Napa, California, pp. 256-261.
Dalvi, et al., "Graph search based detection of periodic activations in complex periodic signals: Application in atrial fibrillation electrograms", In 2015 IEEE 28th Canadian Conference on Electrical and Computer Engineering (CCECE), Halifax, Nova Scotia, Canada, pp. 376-381.
Lin, et al., "Benefits of Atrial Substrate Modification Guided by Electrogram Similarity and Phase Mapping Techniques to Eliminate Rotors and Focal Sources Versus Conventional Defragmentation in Persistent Atrial Fibrillation", JACC: Clinical Electrophysiology, 2016, 2(6): 667-678.
Roney, et al., "Spatial Resolution Requirements for Accurate Identification of Drivers of Atrial Fibrillation", Circ Arrhythm Electrophysiol., 2017, 10(5): e004899 (30 pages).
Ghoraani, et al., "Localized rotational activation in the left atrium during human atrial fibrillation: Relationship to complex fractionated atrial electrograms and low voltage zones", Heart Rhythm, 2013, 10(12): 1830-1838.
Gizurarson, et al., "Hierarchical Schema for Identifying Focal Electrical Sources During Human Atrial Fibrillation: Implications for Catheter-Based Atrial Substrate Ablation", JACC: Clinical Electrophysiology, 2016, 2(6): 656-666.
Hadg Slimane, et al., "QRS complex detection using Empirical Mode Decomposition", Digital Signal Processing, 2010, 20(4): 1221-1228.
Heijman, et al., "The value of basic research insights into atrial fibrillation mechanisms as a guide to therapeutic innovation: a critical analysis", Cardiovascular research, 2016, 109(4): 467-479.
Jacobson, "Auto-threshold peak detection in physiological signals", In Proceedings of the 23rd Annual International Conference of the IEEE Engineering in Medicine and Biology Society, 2001, Istanbul, Turkey, vol. 3, pp. 2194-2195.
Lee, et al., "Epicardial wave mapping in human long-lasting persistent atrial fibrillation: transient rotational circuits, complex wavefronts, and disorganized activity", European Heart Journal, 2014, 35(2): 86-97.
Lee, et al., "Characterization of Foci and Breakthrough Sites During Persistent and Long-Standing Persistent Atrial Fibrillation in Patients: Studies Using High-Density (510-512 Electrodes) Biatrial Epicardial Mapping", Journal of the American Heart Association, 2017, 6(3): e005274 (12 pages).
Lim, et al., "Delineating atrial scar by electroanatomic voltage mapping versus cardiac magnetic resonance imaging: where to draw the line?", Journal of Cardiovascular Electrophysiology, 2014, 25(10): 1053-1056.
Lin, et al., "QRS feature extraction using linear prediction", IEEE Trans Biomed Eng, 1989, 36(10): 1050-1055.
Mehta, et al., "K-means algorithm for the detection and delineation of QRS-complexes in electrocardiogram", IRBM, 2010, 31(1): 48-54.
Miller, et al., "Obesity, Exercise, Obstructive Sleep Apnea, and Modifiable Atherosclerotic Cardiovascular Disease Risk Factors Atrial Fibrillation", J Am Coll Cardiol, 2015, 66(25): 2899-2906.
Narayan, et al., "Clinical Mapping Approach to Diagnose Electrical Rotors and Focal Impulse Sources for Human Atrial Fibrillation", Journal of Cardiovascular Electrophysiology, 2012, 23(5): 447-454.
Nattel, et al., "New ideas about atrial fibrillation 50 years on", Nature, 2002, 415(6868): 219-226.
Ng, et al., "Understanding and Interpreting Dominant Frequency Analysis of AF Electrograms", Journal of Cardiovascular Electrophysiology, 2007, 18(6): 680-685.
Ng, et al., "Iterative method to detect atrial activations and measure cycle length from electrograms during atrial fibrillation", IEEE Trans Biomed Eng., 2014, 61(2): 273-278.
Pandit, et al., "Rotors and the dynamics of cardiac fibrillation", Circ Res., 2013, 112(5): 849-862.
Panoulas, et al., "Enhancement of R-wave detection in ECG data analysis using higher-order statistics", In Proceedings of the 23rd Annual International Conference of the IEEE Engineering in Medicine and Biology Society, 2001, Istanbul, Turkey, vol. 1, pp. 344-347.
Sholkmann, et al., "An efficient algorithm for automatic peak detection in noisy periodic and quasi-periodic signals", Algorithms, 2012, 5(4): pp. 588-603.
Sethares, et al., "Periodicity Transforms", IEEE Transactions on Signal Processing, 1999, 47(11): 2953-2964.
Singh, et al., "A robust R-peak detection algorithm using wavelet packets", International Journal of Computer Applications, 2011, 36(5): 37-43.
Skanes, et al., "Spatiotemporal Periodicity During Atrial Fibrillation in the Isolated Sheep Heart", Circulation, 1998, 98(12): 1236-1248.
Vaquero, et al., "Cardiac fibrillation: From ion channels to rotors in the human heart", Heart Rhythm, 2008, 5(6): 872-879.
Vijayakumar, et al., "Methodology considerations in phase mapping of human cardiac arrhythmias", Circulation: Arrhythmia and Electrophysiology, 2016, 9(11): e004409 (40 pages).
Vivó-Truyols, et al., "Automatic program for peak detection and deconvolution of multi-overlapped chromatographic signals part I: peak detection", J Chromatogr A, 2005, 1096(1-2): 133-145.
Benedetto, et al., "Wavelet detection of periodic behavior in EEG and ECG data", 15th IMACS World Congress, 1997, Berlin, vol. 1, pp. 75-80.
Ganesan, et al., "Long-term outcomes of catheter ablation of atrial fibrillation: a systematic review and meta-analysis", J Am Heart Assoc., 2013, 2(2):e004549 (14 pages).
Quintanilla, et al., "Mechanistic Approaches to Detect, Target, and Ablate the Drivers of Atrial Fibrillation", Circ Arrhythm Electrophysiol., 2016, 9(1): e002481 (11 pages).
Alhusseini, et al., "Two Independent Mapping Techniques Identify Rotational Activity Patterns at Sites of Local Termination During Persistent Atrial Fibrillation", J Cardiovasc Electrophysiol., 2017, 28(6): 615-622.
Heijman, et al., "Cellular and molecular electrophysiology of atrial fibrillation initiation, maintenance, and progression", Circ Res., 2014, 114(9): 1483-1499.
King, et al., "Effect of spatial resolution and filtering on mapping cardiac fibrillation", Heart Rhythm, 2017, 14(4): 608-615.
De Bakker, et al., "Long-Standing Persistent Atrial Fibrillation: Can We Distinguish Ectopic Activity From Reentry by Epicardial Mapping?", Circulation, 2015, 132(22): 2103-2105.
Anter, et al., "High-Resolution Mapping of Postinfarction Reentrant Ventricular Tachycardia: Electrophysiological Characterization of the Circuit", Circulation, 2016, 134(4): 314-327.
Asirvatham, et al., "Editor's perspective: Reentry, pseudo-reentry, and pseudo-pseudo-reentry", Circ Arrhythm Electrophysiol., 2014, 7(3): 557-558.
Haissaguerre, et al., "Intermittent drivers anchoring to structural heterogeneities as a major pathophysiological mechanism of human persistent atrial fibrillation", J Physiol., 2016, 594(9): 2387-2398.
Lim, et al., "Spiral wave attachment to millimeter-sized obstacles", Circulation, 2006, 114(20): 2113-2121.
Lee, et al., "Simultaneous Biatrial High-Density (510-512 Electrodes) Epicardial Mapping of Persistent and Long-Standing Per-

(56) References Cited

OTHER PUBLICATIONS sistent Atrial Fibrillation in Patients: New Insights Into the Mechanism of Its Maintenance", Circulation, 2015, 132(22): 2108-2117.
Luther, et al., "Visualizing Localized Reentry With Ultra-High Density Mapping in Iatrogenic Atrial Tachycardia: Beware Pseudo-Reentry", Circ Arrhythm Electrophysiol., 2017, 10(4): e004724.
Haissaguerre, et al., "Driver domains in persistent atrial fibrillation", Circulation, 2014, 130(7): 530-538.
Narayan, et al., "Treatment of atrial fibrillation by the ablation of localized sources: CONFIRM (Conventional Ablation for Atrial Fibrillation With or Without Focal Impulse and Rotor Modulation) trial", J Am Coll Cardiol., 2012, 60(7): 628-636.
Spach, et al., "Extracellular potentials related to intracellular action potentials during impulse conduction in anisotropic canine cardiac muscle", Circ Res., 1979, 45(2): 188-204.
De Groot, et al., "Direct Proof of Endo-Epicardial Asynchrony of the Atrial Wall During Atrial Fibrillation in Humans", Circ Arrhythm Electrophysiol., 2016, 9(5): e003648 (29 pages).
Shricker, et al., "Human atrial fibrillation initiates via organized rather than disorganized mechanisms", Circ Arrhythm Electrophysiol., 2014, 7(5): 816-824.

\* cited by examiner

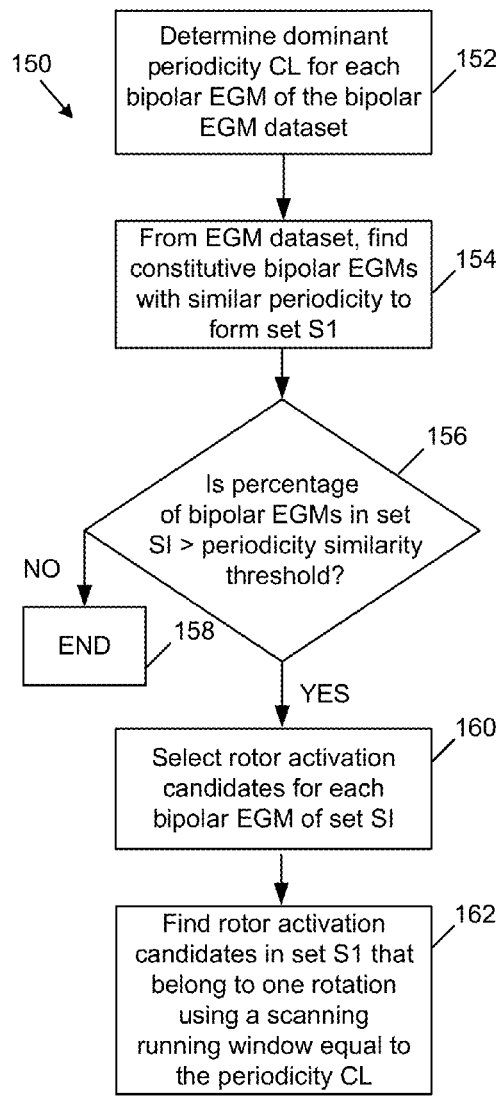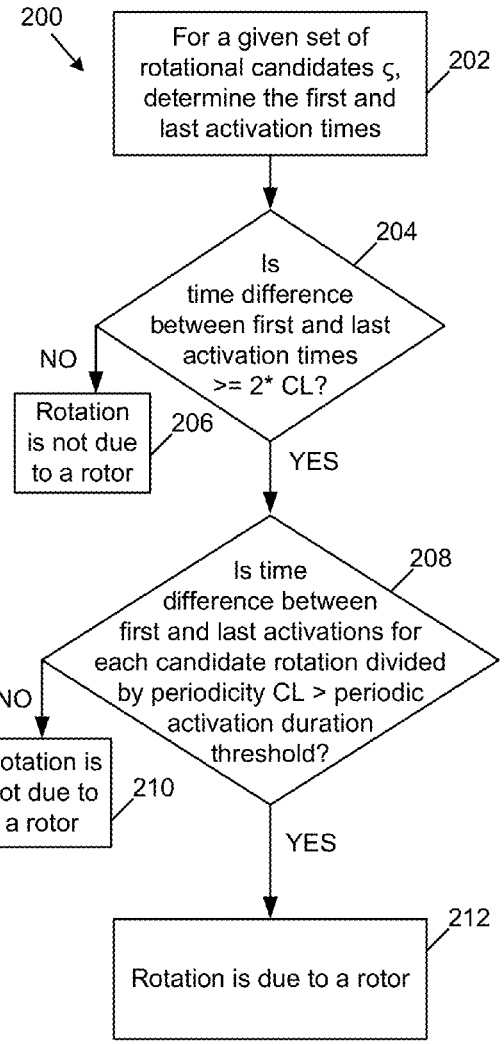
FIG. 6     FIG. 7

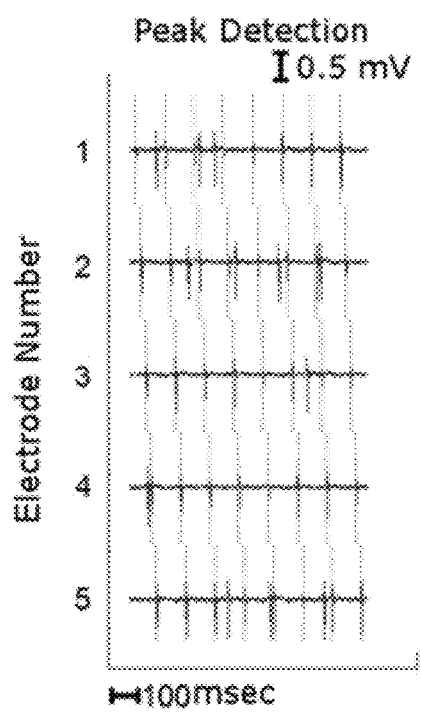 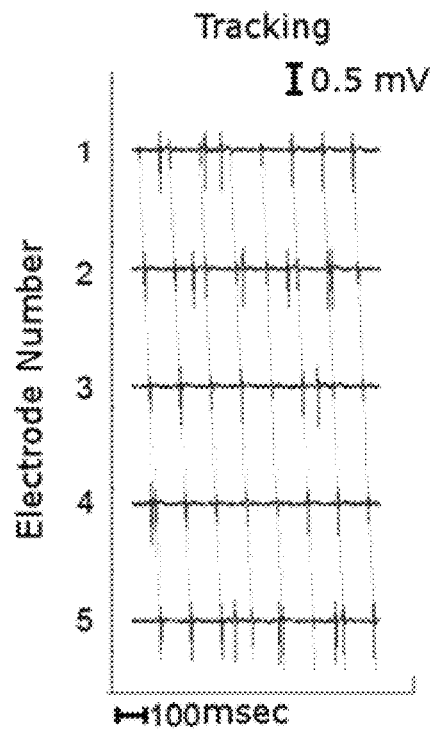
FIG. 15A         FIG. 15B

SYSTEM AND METHOD FOR ROTOR DETECTION IN CARDIAC FIBRILLATION

CROSS-REFERENCE TO RELATED APPLICATION

This application claims the benefit of U.S. Provisional Patent Application No. 62/374,997 filed on Aug. 15, 2016; the entire contents of U.S. Provisional Patent Application No. 62/374,997 are hereby incorporated by reference in its entirety.

FIELD

The various embodiments described herein generally relate to a system and method for detecting rotors in cardiac fibrillation.

BACKGROUND

Atrial fibrillation (AF) is the most common cardiac arrhythmia, affecting millions of patients worldwide, and is a significant cause of morbidity and mortality (Andrade et al., 2014). During normal sinus rhythm, regular electrical impulses travel sequentially from the sinus node (SN) to the right atrium (RA) and then to the left atrium (LA). In AF, electrical propagation is irregular and seemingly chaotic as these electrical impulses travel nonuniformly through the atria resulting in irregular atrial activation. Based on experimental and computational studies, AF can be maintained by rotors, which are rotating or reentrant electrical impulses. For example, it has been hypothesized that human AF is maintained in the heart by a few independent rotors whose periodic impulses breakup remotely in the atria (Vaquero et al., 2008). These rotors represent localized periodic electrical sources from which propagating waves breakup and become more disorganized (Skanes et al., 1998). Ablation of rotors can terminate AF, thereby supporting their role as AF sources (Pandit et al., 2013).

Methods to improve the accuracy of rotor detection may provide therapeutic targets for catheter ablation of AF; thereby improving the success of AF therapy (Ghoraani et al., 2013). However, identifying rotors in patients with AF is quite challenging owing to the complexity and nonstationarity of intracardiac signals. Recently, rotors have been identified using multielectrode basket catheters and phase mapping of unipolar intracardiac electrograms (EGMs) (Narayan et al., 2012). However, this approach has not been reproducible and phase mapping may not be appropriate when signal features become too complex in AF. A more practical approach to rotor detection is to use a circular catheter that conforms to the geometry of a rotor. For instance, a previous study has shown that rotors can be identified in patients with AF using a circular catheter, but the approach requires visual inspection of several hundred bipolar EGMs, which is a tedious process that is not conducive to real-time analysis during AF catheter ablation therapy (Ghoraani et al., 2013).

SUMMARY OF VARIOUS EMBODIMENTS

In a broad aspect, at least one embodiment described herein provides a method of detecting a rotor at a location of a heart that experiences cardiac fibrillation, where the method comprises: obtaining an electrogram (EGM) dataset, where the EGM dataset was recorded using a circular bipolar electrode array positioned at the location of the heart, the circular bipolar electrode array having a plurality of bipolar electrodes for simultaneously recording a plurality of bipolar EGMs for the EGM dataset for a recording duration; detecting a dominant periodicity Cycle Length (CL) and identifying periodic activations for each bipolar EGM associated with the dominant periodicity CL; tracking the identified periodic activations across each bipolar EGM to define rotational activations and determining when a path taken by the tracked rotational activations corresponds to a rotational activation pattern of a rotor; and detecting the rotor when a number and completeness of the tracked rotational activations meet predefined rotor criteria.

In at least one embodiment, the method further comprises performing ablation at the location of the heart when rotor detection occurs at the location.

In at least one embodiment, after ablation the method comprises repeating the acts of obtaining an EGM dataset; determining the dominant periodicity CL and identifying periodic activations, tracking the periodic activations and detecting the rotor; and repeating ablation when the rotor is still detected.

In at least one embodiment, the predefined rotor criteria comprise the tracked rotational activations being greater than at least two complete rotations around the circular bipolar electrode array, that each tracked rotational activation spans across the bipolar EGMs with a time duration where a proportion of the time duration relative to the dominant periodicity CL associated with the rotor is greater than a periodic activation duration threshold and the tracked rotational activations cover a curvature threshold around the circular bipolar electrode array without conduction block.

In at least one embodiment, the dominant periodicity CL is determined by using a method based on one of spectral analysis, autocorrelation, periodicity transforms, periodic component analysis, wavelets, Maximum Likelihood (ML) and Dominant Frequency (DF) analysis.

In at least one embodiment, the periodic activations for a given bipolar EGM are identified by finding peaks in the given bipolar EGM that are associated with the detected dominant periodicity CL by: removing baseline drift and DC bias in the given bipolar EGM; finding a set of peaks ($Peak_{EGM}$) that satisfy a minimum voltage gradient threshold and an absolute amplitude threshold; determining a set of peaks associated with a least cost path on a graph where nodes of the graph of the peaks in $Peak_{EGM}$ and edges of the graph are costs based on a distances between the peaks in $Peak_{EGM}$ relative to the dominant periodicity CL; selecting different potential starting and ending peaks in $Peak_{EGM}$ until end peaks are found that result in the least cost path; and denoting the set of peaks associated with the least cost path as the actual periodic peaks.

In at least one embodiment, the method comprises verifying that the actual periodic peaks contain an initial peak and a final peak for a given EGM by determining costs for various combinations of actual periodic peaks where each combination includes one of n potential initial peaks and one of m potential final peaks; locating the combination with the least cost; and setting the peaks in the located combination as the actual periodic peaks.

In at least one embodiment, tracking the periodic activations across each bipolar EGM to define rotational activations comprises: grouping the EGMs with a similar dominant periodicity CL into an EGM dataset S1; verifying that a percentage of EGMs in the EGM dataset S1 is greater than a periodicity similarity threshold; and determining which periodic activations in the EGM dataset S1 are rotor activation candidates based on the presence of temporal progression of the periodic activations across adjacent bipoles of a circular electrode array.

In at least one embodiment, a current periodic activation $EGM_n$ in an EGM dataset S1 that is unassigned to any candidate rotor is assigned as a rotor activation candidate for a current candidate rotor for a clockwise rotor, when (a) the current periodic activation $EGM_n$ is an earliest periodic activation and the current candidate rotor has no periodic activations assigned to it; or (b) the current periodic activation $EGM_n$ is a nearest periodic activation in a subsequent bipolar EGM and is after, and within, one dominant periodicity CL of a latest periodic activation that was assigned to the current candidate rotor; otherwise, a new candidate rotor is defined when the current periodic activation $EGM_n$ is the nearest annotated periodic activation in a subsequent bipolar EGM that is as yet unassigned to any candidate rotor and is either before the latest periodic activation that was assigned to the current candidate rotor OR after, and more than one dominant periodicity CL away from the latest periodic activation that was assigned to the current candidate rotor and the current periodic activation is assigned to the new candidate rotor.

Alternatively, a current periodic activation $EGM_n$ in an EGM dataset S1 that is unassigned to any candidate rotor is assigned as a rotor activation candidate for a current candidate rotor that is counter-clockwise rotor when: (a) the current periodic activation $EGM_n$ is an earliest periodic activation and the current candidate rotor has no activations assigned to it; or (b) the current periodic activation $EGM_n$ is a nearest periodic activation in a previous bipolar EGM and is before, and within, one dominant periodicity CL of a latest periodic activation that was assigned to the current candidate rotor; otherwise, a new candidate rotor is defined when the current periodic activation $EGM_n$ is the nearest annotated periodic activation in a subsequent bipolar EGM that is as yet unassigned to any candidate rotor and is either after the latest periodic activation that was assigned to the current candidate rotor OR before, and more than one dominant periodicity CL away from the latest periodic activation that was assigned to the current candidate rotor and the current periodic activation is assigned to the new candidate rotor.

In at least one embodiment, when the EGM dataset comprises multiple dominant periodicity CL, the method comprises detecting potential rotors associated with the different dominant periodicity CL and selecting the potential rotor having a greatest number of rotations as the detected rotor.

In at least one embodiment, prior to the act of tracking the identified periodic activations across each bipolar EGM to define rotational activations, the method comprises checking for multiple dominant periodicity CL by: defining a set of current periodic activations associated with the current dominant periodicity CL; removing the set of current periodic activations from the bipolar EGMs; determining if there is an additional dominant periodicity CL; and iterating over the defining, removing and determining acts until all dominant periodicity CL and the associated periodic activations have been found.

In at least one embodiment, for each set of periodic activations associated with a different dominant periodicity CL, the method further comprises performing the acts of tracking the periodic activations and detecting the rotor to detect the potential rotors associated with the different dominant periodicity CL and determining the number of rotations for each potential rotor.

In at least one embodiment, when the dominant periodicity CL is larger than a dominant periodicity threshold the location of the heart is considered too slow to function as a rotor of the cardiac fibrillation.

In at least one embodiment, the method comprises determining when the path taken by the tracked rotational activations corresponds to a wave curvature based on when: the bipolar EGMs of the tracked rotational activation have a similar periodicity CL and a sequential activation that is greater than a rotor activation candidate threshold; and each tracked rotational activation spans across the bipolar EGMs with a time duration where a proportion of the time duration relative to the dominant periodicity CL associated with the rotor is less than a periodic activation duration threshold.

In at least one embodiment, the method comprises determining that a given rotational activation includes local conduction block when an activation time difference between two adjacent bipolar EGMs on the circular bipolar electrode array is greater than a time threshold.

In another aspect, at least one embodiment described in accordance with the teachings herein provides a non-transitory computer-readable medium storing computer-executable instructions, the instructions when executed cause a processing unit to perform a method of detecting a rotor at a location of a heart that experiences cardiac fibrillation, wherein the method comprises: obtaining an electrogram (EGM) dataset, where the EGM dataset was recorded using a circular bipolar electrode array positioned at the location of the heart, the circular bipolar electrode array having a plurality of bipolar electrodes for simultaneously recording a plurality of bipolar EGMs for the EGM dataset for a recording duration; detecting a dominant periodicity Cycle Length (CL) and identifying periodic activations for each bipolar EGM associated with the dominant periodicity CL; tracking the identified periodic activations across each bipolar EGM to define rotational activations and determining when a path taken by the tracked rotational activations corresponds to a rotational activation pattern of a rotor; and detecting the rotor when a number and completeness of the tracked rotational activations meet predefined rotor criteria.

In at least one embodiment for the non-transitory computer readable medium, the predefined rotor criteria comprise: the tracked rotational activations being greater than at least two complete rotations around the circular bipolar electrode array; that each tracked rotational activation spans across the bipolar EGMs with a time duration where a proportion of the time duration relative to the dominant periodicity CL associated with the rotor is greater than a periodic activation duration threshold; and the tracked rotational activations cover a curvature threshold around the circular bipolar electrode array without conduction block.

In at least one embodiment for the non-transitory computer readable medium, tracking the periodic activations across each bipolar EGM to define rotational activations comprises: grouping the EGMs with a similar dominant periodicity CL into an EGM dataset S1; verifying that a percentage of EGMs in the EGM dataset S1 is greater than a periodicity similarity threshold; and determining which periodic activations in the EGM dataset S1 are rotor activation candidates based on the presence of temporal progression of the periodic activations across adjacent bipoles of a circular electrode array.

In at least one embodiment for the non-transitory computer readable, when the EGM dataset comprises multiple dominant periodicity CL, the method comprises detecting potential rotors associated with the different dominant periodicity CL and selecting the potential rotor having a greatest number of rotations as the detected rotor.

In at least one embodiment for the non-transitory computer readable medium, the method comprises determining that a given rotational activation includes local conduction block when an activation time difference between two adjacent bipolar EGMs on the circular bipolar electrode array is greater than a time threshold.

In at least one embodiment, the instructions from the non-transitory computer readable medium, when executed, further cause the processing unit to perform other acts of the method described in accordance with the teachings herein.

In another aspect, at least one embodiment described in accordance with the teachings herein provides an electronic device detecting a rotor at a location of a heart that experiences cardiac fibrillation, the electrical device comprising: an input for obtaining an electrogram (EGM) dataset, where the EGM dataset was recorded using a circular bipolar electrode array positioned at the location of the heart, the circular bipolar electrode array having a plurality of bipolar electrodes for simultaneously recording a plurality of bipolar EGMs for the EGM dataset for a recording duration; a rotor detector coupled to the input to receive the EGM dataset; detect a dominant periodicity Cycle Length (CL) and identify periodic activations for each bipolar EGM associated with the dominant periodicity CL; track the identified periodic activations across each bipolar EGM to define rotational activations and determining when a path taken by the tracked rotational activations corresponds to a rotational activation pattern of a rotor; and detect the rotor when a number and completeness of the tracked rotational activations meet predefined rotor criteria; and an output coupled to the processing unit to output when the rotor is detected and output associated rotor data for a detected rotor.

In at least one embodiment, the device further comprises an ablation unit for performing ablation at the location of the heart where a rotor is detected and after ablation the rotor detector is configured to repeat the acts of obtaining an EGM dataset; detecting a dominant periodicity CL and identifying periodic activations, tracking the periodic activations and detecting the rotor to determine if the ablation was successful.

In at least one embodiment, the device further comprises a sensor unit that includes the circular bipolar electrode array.

In at least one device embodiment, the predefined rotor criteria comprise: the tracked rotational activations being greater than at least two complete rotations around the circular bipolar electrode array; that each tracked rotational activation spans across the bipolar EGMs with a time duration where a proportion of the time duration relative to the dominant periodicity CL associated with the rotor is greater than a periodic activation duration threshold; and the tracked rotational activations cover a curvature threshold around the circular bipolar electrode array without conduction block.

In at least one device embodiment, the rotor detector is configured to track the periodic activations across each bipolar EGM to define rotational activations by: grouping the EGMs with a similar dominant periodicity CL into an EGM dataset S1; verifying that a percentage of EGMs in the EGM dataset S1 is greater than a periodicity similarity threshold; and determining which periodic activations in the EGM dataset S1 are rotor activation candidates based on the presence of temporal progression of the periodic activations across adjacent bipoles of a circular electrode array.

In at least one embodiment, the device further comprises a periodicity filter to separate periodic activations associated with different potential rotors when there are multiple dominant periodicities and to select the potential rotor having a greatest number of rotations as the detected rotor according to certain aspects of the method described herein for detecting rotors when there are multiple periodicities in the bipolar EGMs of an EGM dataset.

In at least one embodiment, the rotor detector is further configured to perform other acts of the method described in accordance with the teachings herein.

In another aspect, at least one embodiment described in accordance with the teachings herein provides an electronic device detecting a rotor at a location of a heart that experiences cardiac fibrillation, the electrical device comprising: an input for obtaining an electrogram (EGM) dataset, where the EGM dataset was recorded using a circular bipolar electrode array positioned at the location of the heart, the circular bipolar electrode array having a plurality of bipolar electrodes for simultaneously recording a plurality of bipolar EGMs for the EGM dataset for a recording duration; a processing unit coupled to the input to receive the EGM dataset; detect a dominant periodicity Cycle Length (CL) and identify periodic activations for each bipolar EGM associated with the dominant periodicity CL; track the identified periodic activations across each bipolar EGM to define rotational activations and determining when a path taken by the tracked rotational activations corresponds to a rotational activation pattern of a rotor; and detect the rotor when a number and completeness of the tracked rotational activations meet predefined rotor criteria; and an output coupled to the processing unit to output when the rotor is detected and output associated rotor data for a detected rotor.

In at least one embodiment, the processing unit is further configured to perform various acts of the rotor detection methods described in accordance with the teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 6 is a flowchart of an example embodiment of a periodic activation tracking method for tracking identified periodic peaks across circular catheter bipoles in order to determine whether the propagation is rotational.

FIG. 7 is a flowchart of an example embodiment of a rotational activation sorting method that may be used to identify sustained and complete rotations for the purpose of rotor detection.

FIG. 15A shows an example of periodicity peak detection in 5 bipolar EGM recordings during AF in a patient.

FIG. 15B shows an example of tracking the periodic peaks of FIG. 15A across adjacent bipoles to detect rotational activation.

Figure 1:
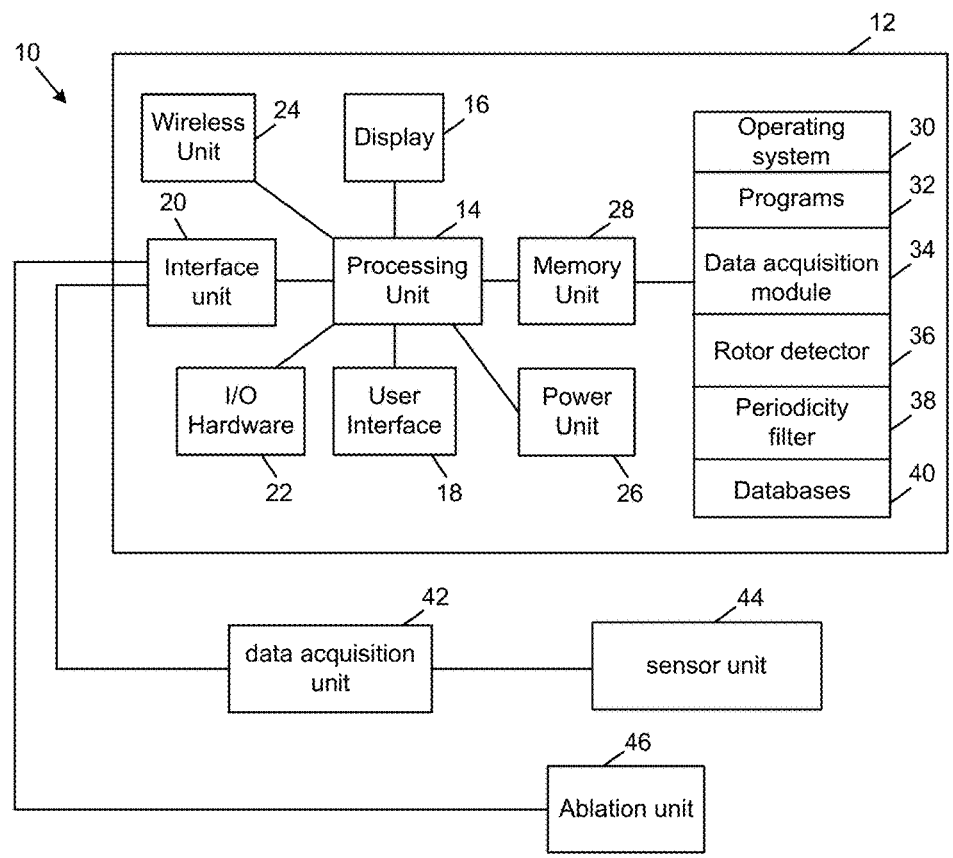
FIG. 1 is a block diagram of an example embodiment of a system that can be used to detect rotors in cardiac fibrillation.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems and or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, electrical signal or a mechanical element depending on the particular context. Furthermore, the term "communicative coupling" indicates that an element or device can electrically or wirelessly send data to another element or device as well as receive data from another element or device.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5% or 10%, for example, as the case may be.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount such as 1%, 2%, 5% or 10%, for example, of the number to which reference is being made if the end result is not significantly changed.

The example embodiments of the systems and methods described in accordance with the teachings herein may be implemented as a combination of hardware or software. In some cases, the example embodiments described herein may be implemented, at least in part, by using one or more computer programs, executing on one or more programmable devices comprising at least one processing element, and a data storage element (including volatile and non-volatile memory and/or storage elements). These devices may also have at least one input device (e.g. a keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level procedural language such as object oriented programming. Accordingly, the program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read (e.g. executed) by the programmable device, configures the programmable device to operate in a new, specific and predefined manner in order to perform at least one of the methods described in accordance with the teachings herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

In accordance with the teachings herein, in one aspect, there is provided an example embodiment of a method for identifying rotors during cardiac fibrillation from bipolar EGM datasets that are recorded using a multielectrode catheter with a circular configured electrode array. The multielectrode catheter can be a circular catheter. In some cases, the multielectrode catheter can be a larger arrangement having a number of subsets of circular configured electrode arrays, such as a basket catheter with 64 or 128 electrodes that contains smaller subsets of circular configured electrode arrays. The method is automated and capable of detecting rotors in near-real time. The method can be used for patients suffering from cardiac fibrillation, which includes AF or ventricular fibrillation. In some embodiments, the method may use dominant frequency-based periodicity detection along with a graph search algorithm to define the most dominant periodic activation set or peaks of interest in an EGM dataset obtained from the bipoles of the circular configured electrode array. The method then generally tracks the activations across the different EGMs in the EGM dataset to determine whether these activations are travelling in a rotational pattern around the electrodes and conform to the rotational pattern of a rotor. The accuracy of the rotor detection method was tested in detecting synthetic rotors on simulated bipolar EGM datasets containing rotor activation corrupted by noise and complex aperiodic signal features. The feasibility of the rotor detection method to detect real rotors during AF in patients undergoing catheter ablation was also tested.

Referring now to FIG. 1, shown therein is a block diagram of an example embodiment of a rotor detection system 10 that can be used to detect one or more rotors in cardiac fibrillation. The system 10 includes an operator unit 12, a data acquisition unit 42, a sensor unit 44, and an ablation unit 46. The system 10 is provided as an example and there can be other embodiments of the system 10 with different components or a different configuration of the components described herein. The system 10 further includes several power supplies (not all shown) connected to various components of the system 10 for providing power thereto as is commonly known to those skilled in the art. In general, a user may interact with the operator unit 12 to record electrical signals, such as bipolar EGM data from a subject or a patient, and then perform data analysis on the recorded EGM data to identify rotors within the patient's heart.

The operator unit 12 comprises a processing unit 14, a display 16, a user interface 18, an interface unit 20, Input/Output (I/O) hardware 22, a wireless unit 24, a power unit 26 and a memory unit 28. The memory unit 28 comprises software code for implementing an operating system 30 and various programs 32, a data acquisition module 34, a rotor detector 36, a periodicity filter 38 and one or more databases 40. Many components of the operator unit 12 can be implemented using a desktop computer, a laptop, a mobile device, a tablet, and the like.

The processing unit 14 controls the operation of the operator unit 12 and can be any suitable processor, controller or digital signal processor that can provide sufficient processing power depending on the configuration, purposes and requirements of the system 10 as is known by those skilled in the art. For example, the processing unit 14 may be a high performance general processor. In alternative embodiments, the processing unit 14 may include more than one processor with each processor being configured to perform different dedicated tasks. In alternative embodiments, specialized hardware can be used to provide some of the functions provided by the processing unit 14.

The display 16 can be any suitable display that provides visual information depending on the configuration of the operator unit 12. For instance, the display 16 can be a cathode ray tube, a flat-screen monitor and the like if the operator unit 12 is a desktop computer. In other cases, the display 16 can be a display suitable for a laptop, tablet or handheld device such as an LCD-based display and the like.

The user interface 18 can include at least one of a mouse, a keyboard, a touch screen, a thumbwheel, a track-pad, a track-ball, a card-reader, voice recognition software and the like again depending on the particular implementation of the operator unit 12. In some cases, some of these components can be integrated with one another.

The interface unit 20 can be any interface that allows the operator unit 12 to communicate with other devices or computers. In some cases, the interface unit 20 can include at least one of a serial port, a parallel port or a USB port that provides USB connectivity. The interface unit 20 can also include at least one of an Internet, Local Area Network (LAN), Ethernet, Firewire, modem or digital subscriber line connection. Various combinations of these elements can be incorporated within the interface unit 20.

The I/O hardware 22 is optional and can include, but is not limited to, at least one of a microphone, a speaker and a printer, for example.

The wireless unit 24 is optional and can be a radio that communicates utilizing CDMA, GSM, GPRS or Bluetooth protocol according to standards such as IEEE 802.11a, 802.11b, 802.11g, or 802.11n. The wireless unit 24 can be used by the operator unit 12 to communicate with other devices or computers.

The power unit 26 can be any suitable power source that provides power to the operator unit 12 such as a power adaptor or a rechargeable battery pack depending on the implementation of the operator unit 12 as is known by those skilled in the art.

The memory unit 28 can include RAM, ROM, one or more hard drives, one or more flash drives or some other suitable data storage elements such as disk drives, etc. The memory unit 28 may be used to store an operating system 30 and programs 32 as is commonly known by those skilled in the art. For instance, the operating system 30 provides various basic operational processes for the operator unit 12. The programs 32 include various user programs so that a user can interact with the operator unit 12 to perform various functions such as, but not limited to, acquiring data, viewing and manipulating data, adjusting parameters for data analysis as well as sending messages as the case may be.

The data acquisition module 34 is used to obtain electrical signals from one or more locations in a patient or a subject, and more particularly from one or more locations within an organ of interest for the patient or subject. For example, in some embodiments, the data acquisition module 34 is operable to acquire signals from at least one region of the patient's heart. The data acquisition module 34 is coupled to the data acquisition unit 42 and the sensor unit 44 in order to acquire these signals.

In some cases, the data acquisition module 34 may be used to obtain electrical signal data from a single location within the heart. In the context of rotor detection, this corresponds to using an array of electrodes positioned in an area or single location within the heart where each electrode provides EGM data and all of the EGM data from the electrode array is referred to collectively as an EGM dataset. In other cases, the data acquisition module 34 may be used to obtain electrical signal data from multiple locations within the heart depending on the sensor unit 44 that is used; for example by using a basket catheter with several electrode subsets where each subset comprises an array of electrodes in a circular configuration and each subset is in a different location within the heart such that there is no cross-talk or other interference between the different subsets of catheter electrodes.

The electrical signals obtained by the data acquisition module 34 can include bipolar EGM from a region of electrically active tissue, such as the atrium or ventricle of a patient's heart, for example. The electrical signals may be preprocessed by the data acquisition unit 42 and transferred to the operator unit 12 through the interface unit 20. The preprocessing that is done may include standard signal processing techniques such as, but not limited to, at least one of amplification, filtering and de-noising (e.g. averaging). The interface unit 20 may be a multichannel data interface coupling the data acquisition unit 42 to the operator unit 12.

It should be noted that while the system 10 is described as having the data acquisition unit 42, the sensor unit 44 and the data acquisition module 34 for acquiring electrophysiological signals, the system 10 may be implemented without these components in an alternative embodiment. This corresponds to situations in which the electrophysiological signals have already been recorded and the system 10 is being used to analyze the recorded electrophysiological signals and provide output information including locations of possible rotors shown in a graphical or numerical format.

The rotor detector 36 processes the data that is obtained by the data acquisition module 34 in order to detect whether there is a rotor at the location of the heart from which the EGM datasets were obtained. Example embodiments of rotor detection methods that may be employed by the rotor detector 36 are described in more detail with respect to FIGS. 3, 4, 5, 6, 7 and 14. The detected rotors may then be provided as an output consisting of an electronic file or a display image with information on the location of the rotors.

The rotor detector 36 can be coupled to a commercially available mapping system, such as the CARTO™ system manufactured by Biosense Webster, or the NAVX™ system manufactured by St. Jude Medical, to annotate locations in the heart of a patient that have been identified as harbouring rotors. Alternatively, the rotor detector 36 may be coupled to a memory element, such as the databases 40 or another data storage element, as is known by those skilled in the art, for analyzing previously recorded electrophysiological signals.

The periodicity filter 38 is used when there is an EGM dataset with multiple periodicities in each bipolar EGM of the EGM dataset in order to detect the most stable rotor with the greatest number of complete rotations of a given dominant periodicity cycle length. The operation of the periodicity filter is described in further detail with respect to FIG. 11.

At least one of the rotor detector 36 and the periodicity filter 38 can be implemented by the processing unit 14. Alternatively, at least one of the rotor detector 36 and the periodicity filter 38 can be implemented by electronic components such as an Application Specific Integrated Circuit (ASIC) or a Field Programmable Gate Array (FPGA) or discrete electronics where appropriate.

In alternative embodiments, the elements 34 to 38 may be combined or may be separated into further elements. The elements 34 to 38 are typically implemented using software, but there may be instances in which they are implemented using FPGA or application specific circuitry. For ease of understanding, certain aspects of the methods described in accordance with the teachings herein are described as being performed by the rotor detector 36 and the periodicity filter 38. It should be noted, however that these methods are not limited in that respect, and the various aspects of the methods described in accordance with the teachings herein may be performed by other elements.

The databases 40 can be used to store data for the system 10 such as system settings, parameter values, and calibration data. The databases 40 can also store other information required for the operation of the programs 32 or the operating system 30 such as dynamically linked libraries and the like.

The operator unit 12 comprises at least one interface that the processing unit 14 communicates with in order to receive or send information. This interface can be the user interface 18, the interface unit 20 or the wireless unit 24. For instance, the various threshold parameters used by the system 10 in order to detect rotors and/or filter multiple periodicities may be inputted by a user through the user interface 18 or they may be received through the interface unit 20 from a computing device. The processing unit 14 can communicate with either one of these interfaces as well as the display 16 or the I/O hardware 22 in order to output data related to rotor location and possibly the threshold parameters and other parameters. In addition, users of the operator unit 12 can communicate data across a network connection to a remote system for storage and/or further analysis in some embodiments. This communication may also include email communication.

The user can also use the operator unit 12 to input information needed for system parameters that are needed for proper operation of the system 10 such as calibration information and other system operating parameters as is known by those skilled in the art. Data that are obtained from tests, as well as parameters used for operation of the system 10, may be stored in the memory unit 28. The stored data may include raw recorded data, preprocessed recorded data as well as rotor detection data and/or multiple periodicity data.

The data acquisition unit 42 comprises hardware and circuitry that is used to record electrical signal sets from a patient or subject. The data acquisition unit 42 may be custom designed or may be implemented using commercially available clinical electrophysiology data acquisition systems and/or three-dimensional electroanatomical mapping systems such as, but not limited to, the CARTO™ system manufactured by Biosense Webster, or the NAVX™ system manufactured by St. Jude Medical, for example.

The sensor unit 44 is used to measure the electrical information from the heart of the patient or subject. The sensor unit 44 can be a multi-electrode sensor such as a 20-electrode circular catheter such as the Lasso™ (Biosense Webster), or the Spiral™ (St. Jude Medical) that can be used to gather electrical information from discrete areas of the heart. In other embodiments, a multi-electrode contact basket catheter can also be used such as the Constellation™ (Boston Scientific).

The ablation unit 46 is optional in some embodiments since not all detected rotors need to be ablated, if for instance they are located in a structure where ablation may be unsafe or result in complications. The ablation unit 46 is used to ablate any or all rotors that have been identified in the patient's heart. The ablation unit 46 can be any suitable ablation unit such as the commercially available Stockert™ ablation generator manufactured by Biosense Webster, for example. Other ablation units may be used if suitable. The ablation unit 46 may be used to deliver heat energy to the heart of the patient at identified ablation targets. For example, a medical practitioner may use the methods described in accordance with the teachings herein to identify rotor locations and to guide ablation at those rotor locations.

Figure 2A:
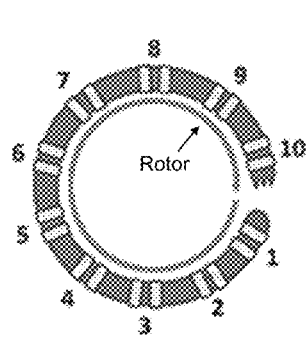
FIGS. 2A-2B show schematics of rotor activity detected by a 10-bipole circular catheter.
Figure 2B:
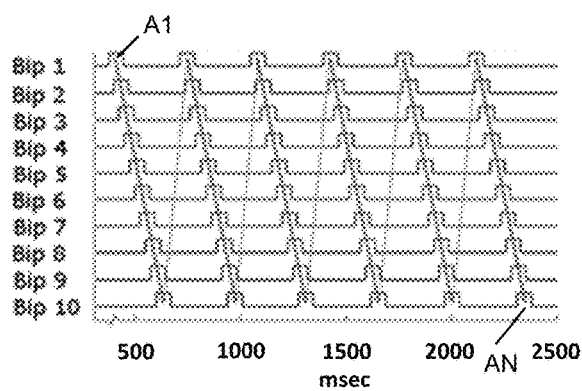

In accordance with the teachings herein, in one aspect, there is provided an example embodiment of a method for identifying rotors from bipolar EGM datasets recorded during cardiac fibrillation using a multipolar circular catheter or basket catheter (with one or more designated circular electrode subarrays). If a circular electrode array is placed over a rotor during cardiac fibrillation, the electrical wave will first be detected by one bipole (i.e. a pair of electrodes acting as a bipolar electrode), then the bipole immediately next to it (in a clockwise or anticlockwise direction depending on the wave direction), and so on until the wave returns to activate the first bipole again. This periodic rotational cycle will repeat so long as the rotor continues to exist. FIG. 2A shows a schematic of 10 bipoles of a circular catheter and the rotor travelling along it. FIG. 2B shows the corresponding bipolar EGMs (Bips—which represents bipoles) against time as seen by the catheter's bipoles. The downward slanting arrows show the wave propagation from bipole 1 to bipole 10. The upward slanting arrows show wave propagation starting again from bipole 10 to bipole 1. The rotor in this example completes six rotations around the circular catheter.

Figure 3:
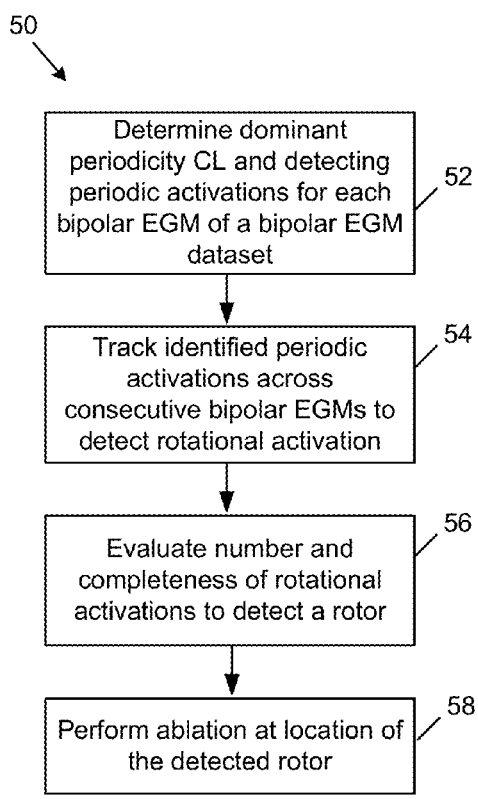
FIG. 3 is a flowchart of an example embodiment of a rotor detection method for detecting rotors in cardiac fibrillation.

Referring now to FIG. 3, shown therein is a flowchart of an example embodiment of a rotor detection method 50. The rotor detection method 50 may be used to identify rotors in clinical situations, such as in patients undergoing AF catheter ablation.

The rotor detection method 50 comprises determining the dominant periodicity CL and using it to detect periodic activations at act 52 for each bipolar EGM of an EGM dataset where the bipolar EGMs are recorded simultaneously from the multielectrode catheter, with a circular electrode array, at a particular sampling location in the patient's heart. Accordingly, these bipolar EGMs are herein collectively referred to as an EGM dataset. Each bipolar EGM can be recorded at prespecified filter settings, for example 30-500 Hz, and at prespecified sampling rates, for example 1000-2000 Hz. The duration of each bipolar EGM recording can be at least a few seconds, for example 5 seconds, in order to permit detection of nonsustained or sustained rotor activity at a particular sampling location in the patient's heart.

At act 54, the detected periodic activations from each bipolar EGM of the EGM dataset are tracked across consecutive bipoles (obtained from adjacent electrodes in the circular electrode array) to determine whether their path conforms to the rotational activation that is inherent to a rotor.

At act 56, the completeness and number of rotational activations are evaluated in order to detect a rotor. Accordingly, a first predefined rotor criterion to define a rotor is that rotational activation around the circular electrode array must be complete such that the time interval spanned by the periodic activations in the circular electrode array must be greater than a periodic activation duration threshold which is a percentage of the dominant periodicity cycle length (CL). In other words, the time interval spanned by the periodic activations as a proportion of the dominant periodicity CL associated with the rotor is greater than the periodic activation duration threshold. An incomplete rotation is not considered a rotor but rather passive wave curvature. Accordingly, a second predefined rotor criterion to define a rotor is that at least two complete rotations around the circular electrode array must be satisfied. Thus, only one rotation around the circular electrode array is not sufficiently stable to be considered a rotor.

In some embodiments, the rotor detection method 50 may contain an additional act 58, which is optional, and during which ablation is performed at the location of the detected rotor in the patient's heart. Rotors have been shown to drive AF in experimental and computational studies. Ablation of these rotors in experimental and computational studies terminates AF, which supports their role in driving AF. In human AF, the detection of rotors may provide therapeutic targets for catheter ablation in the management of patients with AF. Ablation of rotors detected with the method 50 may terminate AF or reduce the risk of AF recurrence in patients.

After rotor ablation is performed at act 58, acts 52 to 56 may be repeated to determine if the detected rotor no longer exists. If additional rotors are detected then the area of the heart corresponding to the location of these rotors may be further ablated at act 58.

Regardless of whether act 58 is performed or not, the method 50 may further comprise providing an output when the rotor is detected where the output includes associated rotor data for the detected rotor. The associated rotor data can include at least one of the location of the heart where the rotor was detected, the robustness of the rotor in terms of the number of complete rotations that were observed and the dominant periodicity CL associated with the detected rotor. In the case of multiple potential rotors due to multiple dominant periodicity CL (see method 250 and FIG. 11), this data can be provided for each of the potential rotors.

Periodic activation detection, in act 52, comprises identifying periodic activations or peaks in each bipolar EGM of the EGM dataset that is recorded by the circular electrode array. Several peak detection algorithms may be used for this purpose, which employ a variety of properties and techniques, including window-thresholding (Jacobson, 2001), K-Means clustering (Mehta et al., 2010), wavelet transform (Singh et al., 2011) and periodicity transforms (Sethares et al., 1999) and periodic component analysis. Some recent peak detection methods, such as (Scholkmann et al., 2012) improve the peak detection process by using non-parametric approaches. However, most of these peak detection algorithms assume that (i) all valid peaks are peaks of interest and not specifically those that correspond to a periodic activity, and (ii) peaks of interest have to be local maxima. In contrast, the inventors have found that in rotor detection, neither assumption is valid. In particular, the inventors have found that the rotor peaks of interest should be periodic, but may not have the largest local amplitude. Furthermore, the EGMs in the EGM dataset may be contaminated by aperiodic pulses that are local maxima, and thus while being genuine peaks, are not part of any sequence. These signal features will compromise the ability of most conventional peak detection methods to find periodic peaks of a particular periodic CL in the recorded EGM dataset.

The limitations of the conventional peak detection methods may be overcome by using a peak detection algorithm (Dalvi et al., 2015) that identifies periodic peaks in signals with both periodic and aperiodic components by employing dominant frequency-based periodicity detection along with a graph search algorithm to identify periodic peaks of interest.

Figure 4:
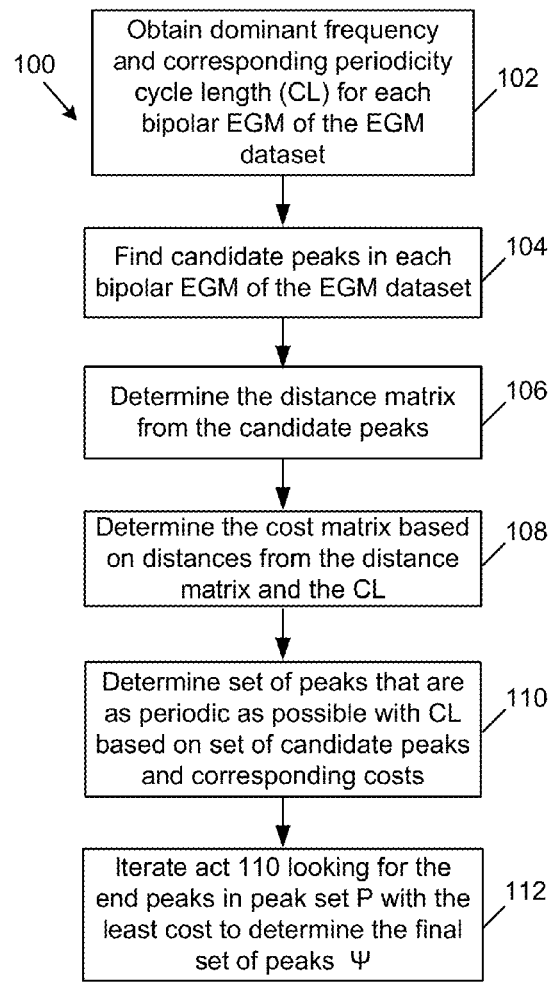
FIG. 4 is a flowchart of an example embodiment of an activation detection method that may be used to detect and annotate periodic activations in a bipolar EGM of a bipolar EGM dataset.

Referring now to FIG. 4, shown therein is a flowchart of an example embodiment of a periodic activation detection method 100 that may be used to detect periodic activations in each bipolar EGM of the EGM dataset. This involves determining the periodic peaks in each bipolar EGM of the EGM dataset that correspond to the respective dominant periodicity CL of each bipolar EGM. The method 100 is applied to each EGM dataset where each EGM dataset is obtained from the multi-electrode sensor 44 positioned in a particular location within the patient's heart.

At act 102, the dominant frequency (DF) for each bipolar EGM in the EGM dataset is obtained as well as the corresponding dominant periodicity CL. Dominant frequency identification can be done using a variety of methods such as methods based on at least one of spectral analysis, autocorrelation, periodicity transforms (Sethares et al., 1999), periodic component analysis, wavelets (Benedetto et al., 1997), and Maximum Likelihood (ML) approaches (Dalvi et al., 2013).

In this example embodiment, DF analysis is used to find the dominant periodicity CL. DF analysis has been widely adopted in AF EGM analysis (Skanes et al., 1998; Pandit et al., 2013; Ng et al., 2007). The DF analysis comprises bandpass filtering (for example at 40-250 Hz) each bipolar EGM in the EGM dataset to augment the sinusoidal waveforms and then rectifying and further low pass filtering (for example at 20 Hz) the filtered bipolar EGM. A third order Butterworth filter can be used for filtering, for example. Then, the most powerful frequency in the power spectral density (PSD) distribution of the rectified filtered bipolar EGM is considered the 'dominant' frequency'. If the power of the most dominant frequency is greater than a power spectral threshold, for example 10-15%, of the power of the whole PSD distribution, then the method 100 proceeds to act 104, otherwise the method 100 ends. The power spectral percentage threshold is selected empirically to ensure that a sufficiently periodic bipolar EGM is detected.

At act 104, the set (i.e. Peak$_{EGM}$) of all candidate periodic peaks in the EGM dataset is found. Act 104 begins by removing baseline drift and DC bias in each bipolar EGM of the EGM dataset, which is then represented by bipolar EGM dataset S. The drift may be determined by fitting (e.g. in a least squares sense) a third order polynomial to the signal and subtracting it. Candidate periodic peaks are peaks which satisfy two criteria, namely a minimum voltage gradient threshold and an absolute amplitude threshold. The voltage gradient refers to the rate of change of bipolar EGM voltage over time and indicates the sharpness of the peaks, which is an indication of healthy heart tissue and/or proximity of the recording bipolar electrode to the surface of the heart. A voltage gradient threshold greater than 0.01 mV/msec, for example, can be empirically selected to indicate peaks in non-scar heart tissue and/or close proximity of the recording bipolar electrode to the surface of the heart. The absolute amplitude threshold refers to the size of the bipolar EGM, and indicates healthy heart tissue. An absolute amplitude threshold greater than 0.05 mV, for example has been used in published literature to indicate peaks in non-scar heart tissue.

At act 106, the process of identifying actual periodic peaks among the candidate periodic peaks begins, based on the periodicity CL derived in act 102. Act 106 begins by obtaining a distance matrix according to equation (1):

$$Peak_{Distances} = \begin{bmatrix} |P(1) - P(1)| & \dots & |P(1) - P(N)| \\ \vdots & \ddots & \vdots \\ |P(N) - P(1)| & \dots & |P(N) - P(N)| \end{bmatrix} \quad (1)$$

where P(N) is the $N^{th}$ peak in the set of candidate peaks $Peak_{EGM}$.

At act 108, the cost matrix is derived according to equation (2):

$$Peak_{Cost} = \begin{bmatrix} |Peak_{Dist}(1, 1) - CL| & \dots & |Peak_{Dist}(1, N) - CL| \\ \vdots & \ddots & \vdots \\ |Peak_{Dist}(1, N) - CL| & \dots & |Peak_{Dist}(N, N) - CL| \end{bmatrix} \quad (2)$$

where $Peak_{Dist}(n,m)$ is the distance from the peak at node n to the peak at node m in the peak candidate dataset $Peak_{EGM}$. The values in the cost matrix $Peak_{cost}$ correspond to the deviation of the distance between any two peaks from the periodicity CL.

At act 110, the least cost path is determined between the first and last element in $Peak_{EGM}$ (where all the $Peak_{EGM}$ elements are nodes on a graph and corresponding $Peak_{Cost}$ elements are edge weights). The rationale behind doing so is that the costs in $Peak_{Cost}$ indicate how much the distance between any two peaks differs from the dominant periodicity CL. Hence, the shortest cost path is the path that returns a set of peaks (P') which are as periodic as possible with a periodicity equal to the dominant periodicity CL. The set of peaks P' contains any and all peaks that constitute the least cost path. These may contain peaks which are isolated, and far away from other peaks on either side. Such peaks may be far more than a periodicity CL away from the nearest peaks on either side. They may not legitimately be considered part of a sequence, but peaks that are merely chosen to reduce the overall cost of the path. These points are removed. Hence peaks from P' are included in the final set of peaks (P) which are about one periodicity CL (within a periodicity proximity threshold of the periodicity CL, for example 10-15%) away from another peak in the set P'. A periodicity proximity threshold of 10-15% is selected empirically to improve selection of periodic peaks that may be very close to the periodicity CL.

However, the final periodic sequence (e.g. set of final peaks P) associated with the determined dominant periodicity CL may not contain the end peaks in the candidate peaks $Peak_{EGM}$ selected from the bipolar EGM dataset S. To account for this, act 112 includes iterating over act 110 to look at the n initial peaks in the set $Peak_{EGM}$ as the first peak and the m final peaks in the set $Peak_{EGM}$ as a last peak. The parameters n and m are integers and they can be the same or different. For example, n and m can be set to 4, or in some embodiments they can be set to 3. The value of n is selected to be large enough to make it more likely that an end peak is included in this analysis, but small enough that this analysis is not overly computationally expensive. The first/last peak combination which results in the least cost for the final set of peaks P is chosen. The peak set corresponding to this combination is considered the final peak set ($\Psi$) that corresponds to the dominant periodicity CL.

Figure 5:
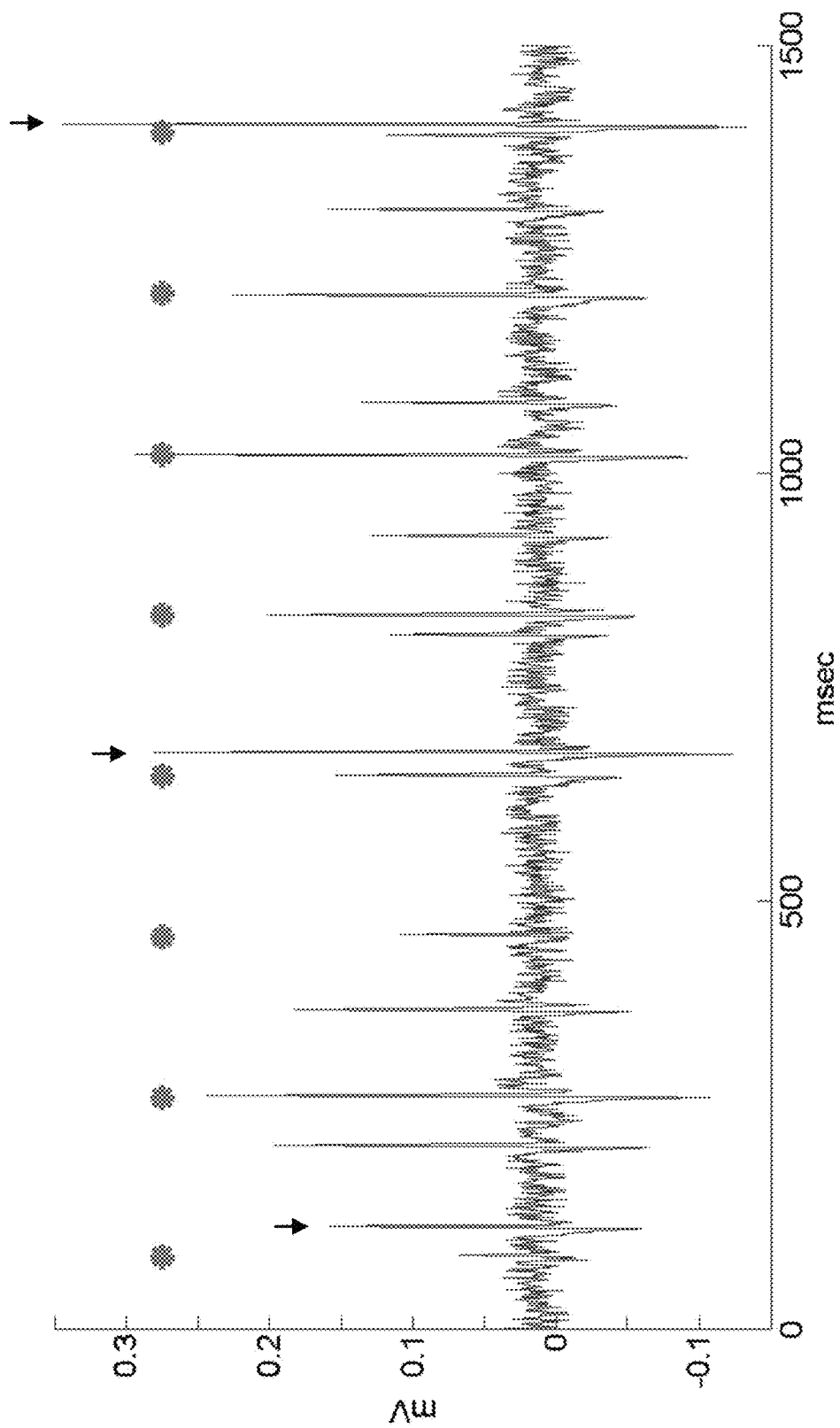
FIG. 5 shows the performance of the activation detection method of FIG. 4 on a simulated AF bipolar EGM containing a periodic pulse sequence (periodicity cycle length 186 msec), shown by the asterisks, interspersed with aperiodic peaks (i.e. aperiodic activations).

FIG. 5 shows the result of the activation detection method 100 on a simulated AF bipolar EGM containing a periodic pulse sequence (dominant periodicity CL 186 msec) interspersed with aperiodic peaks (i.e. aperiodic activations). The asterisks indicate the periodic activations detected by the activation detection method 100 which correspond to all visually apparent periodic activations. Of note, the method 100 does not annotate aperiodic peaks, even if they are larger in amplitude than the periodic peaks. The arrows indicate aperiodic peaks with larger amplitudes than neighboring periodic peaks. These aperiodic peaks are not selected by the method 100.

Once the periodic peaks are detected, each peak is tracked across the bipoles of the circular electrode array in order to determine whether propagation is rotational as depicted in FIGS. 2A-2B. This corresponds to act 54 of method 50 and method 150 as shown in FIG. 6. In one example embodiment, in accordance with the teachings herein, the following features are evaluated to determine whether rotational activation is present:

1) the bipolar EGMs of the EGM dataset must have a similar dominant periodicity CL with an acceptable variation, that variation being, for example within a periodicity variation threshold of 5-10% of the median dominant periodicity CL of the EGM dataset. This can be determined by acts 152 and 154 of method 150 for all bipolar EGMs of the EGM dataset;

2) a majority of the bipolar EGMs of the EGM dataset obtained from the circular electrode array are included in terms of having a similar dominant periodicity CL; for example at least a periodicity similarity threshold of 70-80% of the bipolar EGMs in the EGM dataset. This can be determined by act 156 of method 150. If this condition is not true then the method 150 can end at act 158; and 3) rotational activation travels monotonously from the first bipole to the last bipole in the circular electrode array before returning to the first bipole which implies that the activation in any given bipole will be after the corresponding activation in the preceding bipole and before the corresponding activation in the subsequent bipole, where for the first bipole in the circular electrode array the previous bipole will be the last bipole in the circular electrode array, and vice versa. This assessment of rotational activation can be determined by acts 160 and 162 of method 150.

Referring now to FIG. 6, shown therein is a flowchart of an example embodiment of a periodic activation tracking method 150 for tracking the identified periodic peaks across the catheter bipoles in order to determine whether the propagation is rotational (Dalvi et al 2015, Dalvi et al 2016a). At act 152, the method 150 comprises determining the dominant periodicity CL for each bipolar EGM of the bipolar EGM dataset.

At act 154, the method 150 determines which bipolar EGMs in the EGM dataset have similar dominant periodicity CL. These bipolar EGMs constitute set S1, which may represent the entire EGM dataset or a portion thereof. For example, the bipolar EGMs with a similar dominant periodicity CL may be determined as those having a dominant periodicity CL that is within a periodicity proximity threshold, X %, of the median dominant periodicity CL of all of bipolar EGMs in the EGM dataset. The periodicity proximity percentage threshold X % may be set to 5-10% as determined empirically.

At act 156, the method 150 determines if the number of bipolar EGMs in set S1, with similar dominant periodicity CL, is greater than a periodicity similarity threshold of the total number of bipolar EGMs within the EGM dataset. If this condition is true, then the method 150 proceeds to act 160. Otherwise, the method 150 ends at act 158 as there are not enough bipolar EGMs with similar periodicity CL to confidently define rotational activation. A periodicity similarity threshold that is a percentage is chosen since, if rotational activation exists, while its periodic activations should be measurable by all of the bipoles of the circular electrode array, the rotational activation may not be measured by a few of the bipoles due to poor electrode contact or instability. The periodicity similarity threshold may be set to 70-80% as determined empirically.

At act 160, the periodic peaks that may arise from rotational activation (i.e. rotor activation candidates) are selected from each bipolar EGM that comprises set S1. A periodic peak (i.e. a periodic activation) in a given bipolar EGM, $EGM_n$, in the set S1, can be selected as a rotor activation candidate based on the presence of temporal progression across adjacent bipoles of a circular electrode array which can be determined using the following criteria:
 a) Unless $EGM_n$ is the first activation in the EGM set $S_1$, find the nearest annotated periodic activation in the previous bipolar EGM which is before, and within, one CL of $EGM_n$. If it is after $EGM_n$, then $EGM_n$ is not a valid rotor activation candidate.
 b) Unless $EGM_n$ is the last activation in the EGM set $S_1$, find the nearest annotated periodic activation in the subsequent bipolar EGMs which is after, and within, one CL of $EGM_n$. If it is before $EGM_n$, then $EGM_n$ is not a valid rotor activation candidate.
 c) If $EGM_n$ is not disqualified under criteria a) or criteria b), then $EGM_n$ is considered as a rotor activation candidate.

The criteria described are for clockwise rotational activation in the circular electrode array as per the example shown in FIG. 2. For anticlockwise rotational activation, the criteria can be reversed. The criteria may first be checked assuming clockwise rotational activation and if no rotor activation candidates are found, the criteria may then be checked assuming counter-clockwise rotational activation.

At act 162, a running window having a width equal to the median dominant periodicity CL is scanned across all of the bipolar EGMs in set S1. If the number of rotor activation candidates across all bipoles in set S1 in the window is greater than a rotor activation candidate threshold, then all of these rotor activation candidates can be considered as belonging to one rotation. For example, the rotor activation candidate threshold may be 70-80%. The rationale for the rotor activation candidate threshold is heuristic and accounts for signal dropout as described in act 156.

Referring again to FIG. 3, act 56 of the rotor detection method 50 comprises determining the number and completeness of rotational activations to detect a rotor. In an example embodiment, this may be done by determining if all of the following additional criteria are satisfied:
 1) at least two consecutive rotations are present to indicate temporal stability of the rotor; and
 2) each rotation is complete, such that the CL spanned across the recording bipoles encompasses the majority of the median dominant periodicity CL, for example a periodicity similarity threshold of 70-80% of the median dominant periodicity CL.

These two criteria remove nonsustained and incomplete rotations from further consideration since the activation in these cases are not due to a rotor, but rather due to a passive phenomenon such as wave curvature (for a single complete rotation or incomplete rotations), for example.

Referring now to FIG. 7, shown therein is a flowchart of an example embodiment of a rotational activation sorting method 200 that may be used to identify sustained and complete rotations for the purpose of rotor detection. Act 202 of the method 200 includes determining the first and last activation times for a given set of consecutive rotations, $\zeta$ of a potential rotor. FIG. 2B shows an example of a first activation $A_1$ and a last activation $A_N$ of a set of consecutive rotations $\zeta$. It should be noted that $A_N$ is not the last activation of one rotation, but rather the last activation of $\zeta$.

At act 204, if the first and last activation times in $\zeta$ are separated by $\geq 2*CL$, then the method 200 proceeds to act 208. Otherwise, the method 200 proceeds to act 206 where $\zeta$ is not considered to be a rotor, having fewer than two rotations, and is discarded. In this example embodiment, a rotor is present if it has at least two consecutive rotations.

At act 208, it is determined whether the time difference between the first and last activation of each candidate rotation in $\zeta$ spans a certain percentage of the median dominant periodicity CL (i.e. median periodicity CL of the bipolar EGMs in set S1) by subtracting the times of the first and last activation of each candidate rotation and obtaining a rotational activation time, dividing the rotational activation time by the median dominant periodicity CL and comparing the division result to the periodic activation duration threshold in order to determine if each candidate rotation is considered as being complete and indicative of a rotor. In other words, if N is the number of bipoles in EGM dataset S1, the time difference between a given activation (say activation n) and the activation n+N−1 is determined (where n+N−1 indicates one rotation). If there is no activation n+N−1, the latest activation available before it is used. This subtraction process is repeated for each candidate rotation in $\zeta$. The rotational activation time for each rotation, td, is then divided by the median dominant periodicity CL and if td/median dominant periodicity CL>the periodic activation duration threshold for each rotation, then a rotor exists. The periodic activation duration threshold may be 70-80%, for example. As before, the rationale for the periodic activation duration threshold is heuristic and accounts for potential signal dropout from a few bipoles of the circular electrode array.

If the determination at act 208 is not true then the method 200 moves to act 210 where the candidate rotations in $\zeta$ are labelled as not being due to a rotor and are discarded. If the determination at act 208 is true, then the method 200 moves to act 212 where the candidate rotations in $\zeta$ are labelled as being due to a rotor.

For acts 202 to 212, the presence of consecutive, complete rotations during the entire recording period, for example 5 seconds, defines a sustained rotor. If rotations spontaneously terminate, but there are still two consecutive, complete rotations that later reinitiate, then a nonsustained rotor is present. In other words, nonsustained rotors are defined as rotors that start and stop during the duration of the recording, for example 5 seconds. Whether a rotor is sustained or nonsustained, it is considered to be the same rotor. The rotor's location in the heart is unique and based on the location of the circular electrode array.

Validation Using Simulated Periodic Signal and Rotors

To test the performance of the proposed rotor detection method 50, 1500 synthetic EGM datasets were generated, half with simulated rotors and half without (Dalvi et al 2016a). Each EGM dataset included 10 bipolar EGMs as is recorded by a 10-bipole circular catheter in actual clinical practice. The EGM datasets containing a rotor had simulated periodic pulse trains of identical periodicity CL (186 msec) that were staggered temporally from one bipole channel to the next (e.g. see FIGS. 8A and 8B). In contrast, the EGM datasets that did not contain a rotor had periodic pulse trains without any particular temporal relationship across the bipolar EGMs (e.g. see FIG. 8C). Each pulse of the pulse train was derived from a template bipolar EGM recorded during AF from a patient undergoing AF catheter ablation.

Figure 8A:
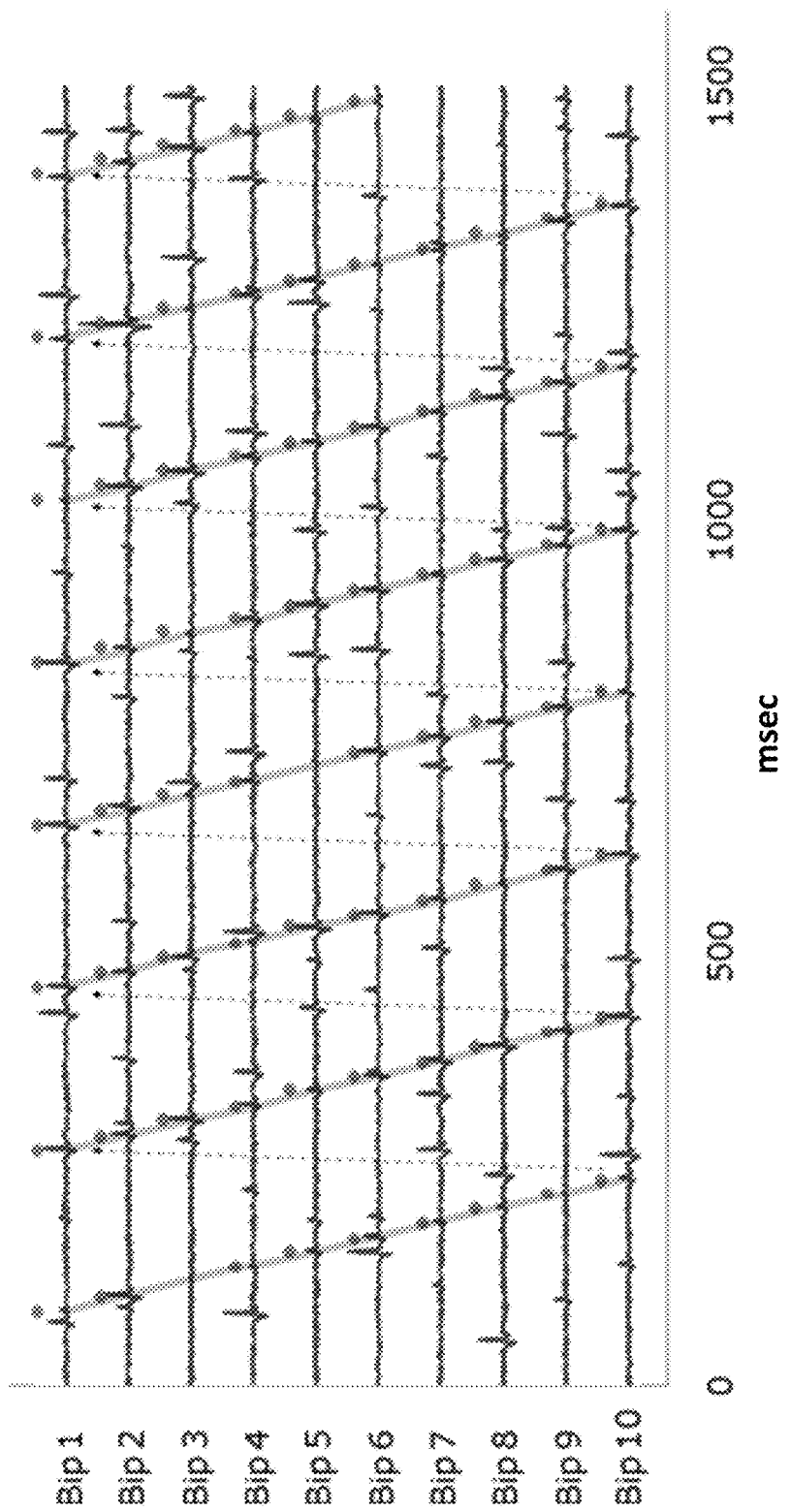
FIG. 8A shows a sampled EGM dataset, containing 10 bipolar EGMs, with a simulated sustained rotor (as indicated by the slanting lines) that were correctly tracked using the rotor detection method of FIGS. 3, 4, 6 and 7 (asterisks indicate periodic activations).
Figure 8B:
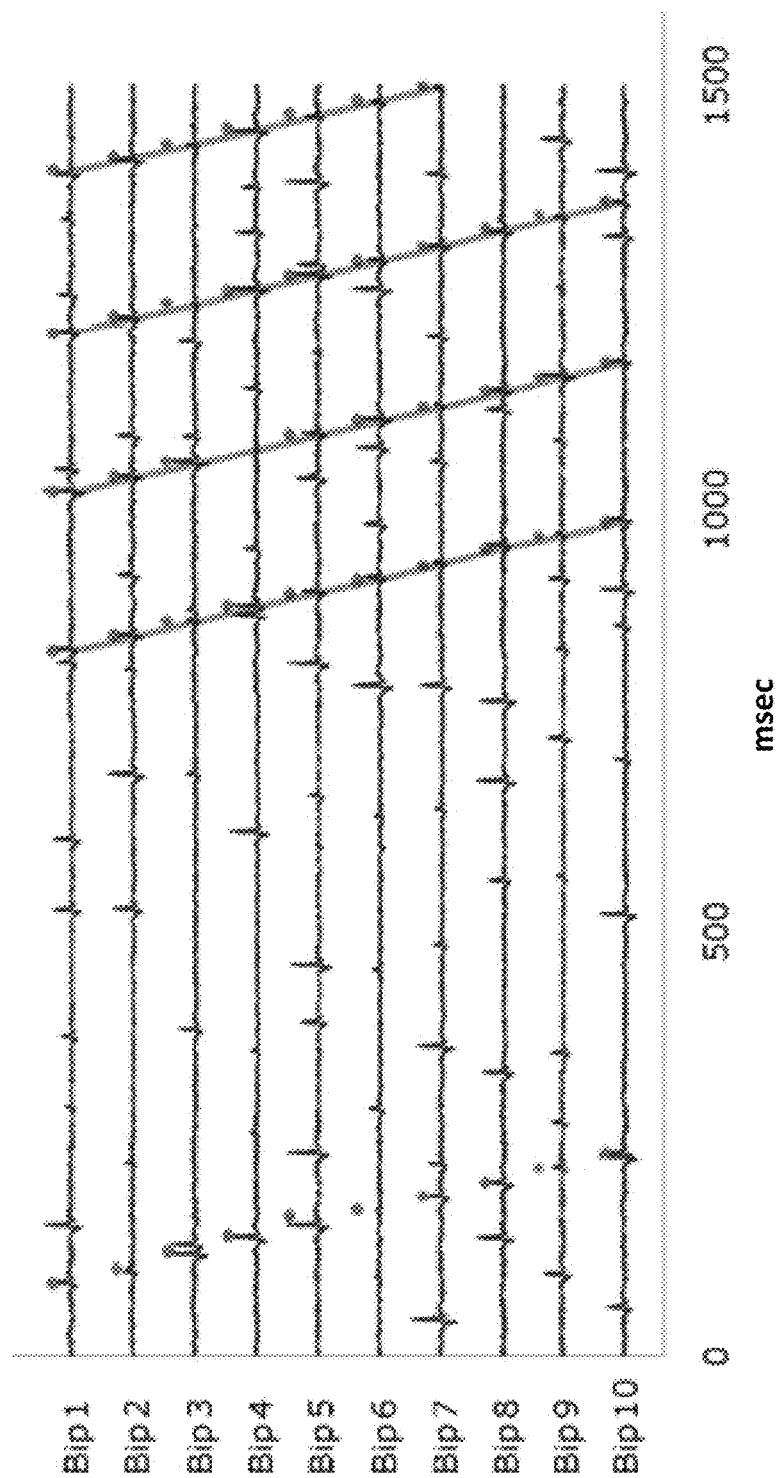
FIG. 8B shows a sampled EGM dataset, containing 10 bipolar EGMs, with a simulated single rotation to the far left and a nonsustained rotor (as indicated by the slanting lines) in the latter half of the EGM dataset (asterisks indicate periodic activations).

Of the 750 EGM datasets with rotor activity, half had sustained rotor activity (i.e. repetitive, consecutive rotations across the 1500 msec bipolar EGM as shown in FIG. 8A) and the other half had nonsustained rotor activity (i.e. rotations terminate and restart across the 1500 msec bipolar EGM as shown in FIG. 8B). The 375 nonsustained rotors were further divided into 3 equal groups with 2, 4 and 6 rotations, respectively.

The periodic pulse trains of each bipole in the array had pulses of varying amplitude (including zero to simulate 'dropped' pulses from poor bipole contact with the atrium). In addition, varying numbers of aperiodic pulses (e.g. 5, 10 and 15) of different amplitudes were added to each periodic pulse train to simulate the complex signal features inherent in AF bipolar EGMs. Since intracardiac EGMs typically have low noise, low amplitude white noise (3 dB SNR) was added to each pulse train.

The performance of method 50 was assessed by its ability to detect simulated rotors in these 1500 EGM arrays. For each array, the method 50 determined if a rotor was present (i.e. true positive) or absent (i.e. true negative). The performance was described in terms of specificity (true negative/(true negative+false positive)) and sensitivity (true positive/(true positive+false negative). The proposed method 50 was programmed using MATLAB 2012b (MathWorks Inc., Natick, Mass., USA) on an Intel W3503 CPU (2.4 GHz) with 6 GB RAM. The analysis time to detect rotors was <1 second per 10 bipole EGM dataset.

Figure 8C:
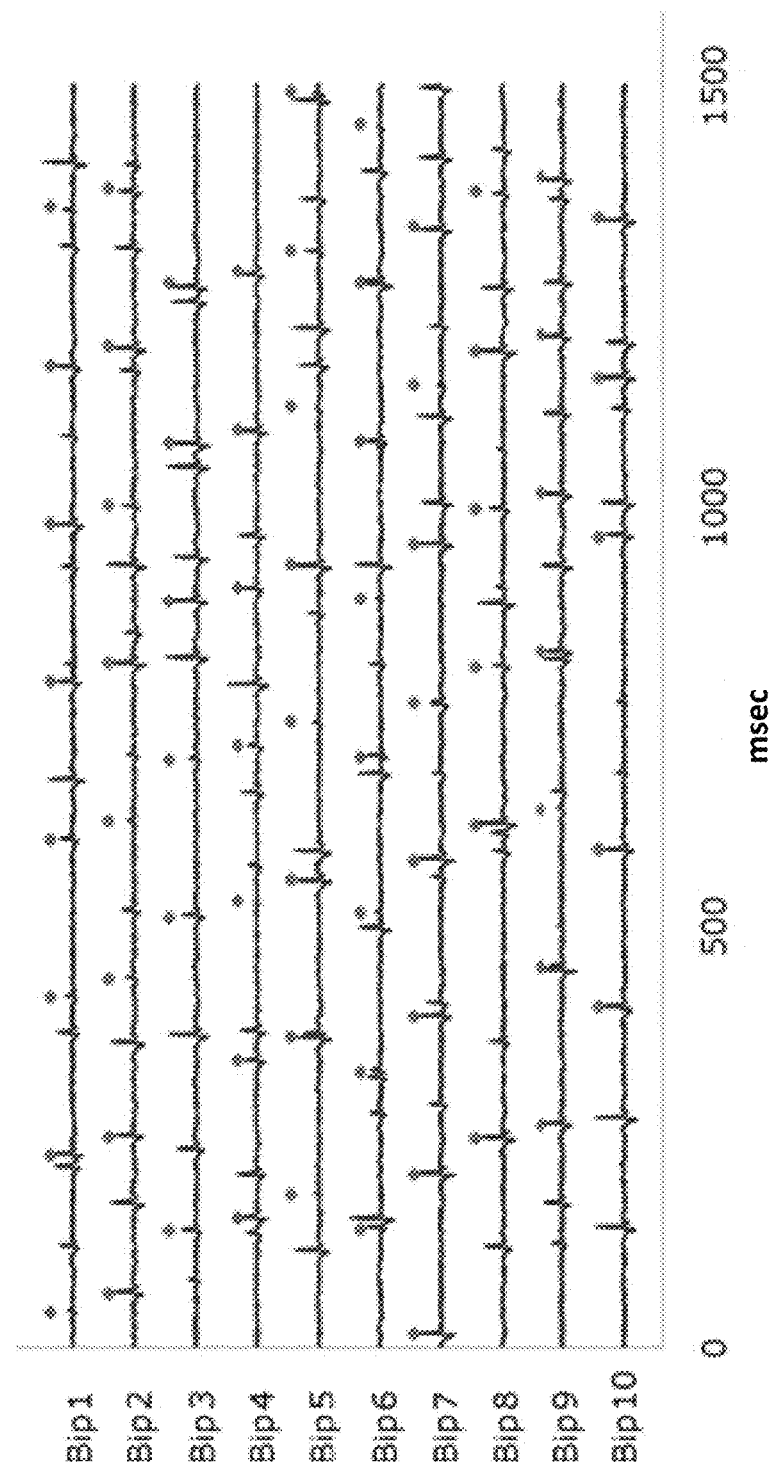
FIG. 8C shows a sampled EGM dataset, containing 10 bipolar EGMs, without a simulated rotor and no detection of a simulated rotor (asterisks indicate periodic activations).

Table I tabulates the performance of the rotor detection method 50 in detecting simulated rotors with increasing numbers of contaminating aperiodic peaks. Table II tabulates the performance of the rotor detection method 50 in detecting simulated nonsustained rotors with a different number of rotations. FIG. 8A shows that the sampled EGM arrays with a simulated sustained rotor were correctly tracked using the method 50 as shown by the slanted lines despite the sampled EGM datasets contaminating aperiodic pulses. FIG. 8B shows a simulated single rotation to the far left and a nonsustained rotor (as indicated by the slanting lines) in the latter half of the array. The rotor detection method 50 identifies the rotor to the right where there are >2 rotations (shown by the slanted lines). In contrast, while the single rotation to the left has rotor activations, it has insufficient rotations to indicate a rotor. FIG. 8C does not show the detection of a simulated rotor. Although periodic activations are detected, no rotor is detected. The asterisks in FIGS. 8A-8C indicate periodic activations which are present in all bipolar EGMs.

TABLE I

Performance in detecting rotor with varying aperiodic peak number

| | # of Aperiodic Peaks | | |
|---|---|---|---|
| | 5 | 10 | 15 |
| Sensitivity | 98 | 85 | 74 |
| Specificity | 100 | 100 | 98 |

TABLE II

Performance in detecting rotor with varying number of rotations

| (SNR 3 dB, # of | # of Rotations | | |
|---|---|---|---|
| aperiodic peaks = 5) | 2 | 4 | 6 |
| Sensitivity | 16 | 89 | 98 |
| Specificity | 100 | 100 | 100 |

Pilot Application in Patients with Atrial Fibrillation

The method 50 was also applied to bipolar EGM datasets recorded from patients with AF in order to evaluate feasibility in detecting real rotors. Patients undergoing AF catheter ablation were prospectively enrolled (n=10, median age 62 years, 8 males, 2 females). The left atrium was accessed using the standard transeptal approach after femoral venous cannulation. A 20-pole circular catheter (Lasso™, Biosense Webster) with 10-bipolar electrode pairs was maneuvered to 40-50 anatomically distinct locations in the left atrium. At each site, a 10-bipolar EGM dataset was simultaneously recorded (using a sampling rate of 1,024 Hz, and bandpass filtering of 30-500 Hz) during AF on a commercial mapping system (CARTO3™, Biosense Webster) and exported for off-line analysis of rotors using the rotor detection method 50. The clinical study was approved by the University Health Network Research Ethics Board and all patients provided written informed consent.

For the pilot clinical study, bipolar EGMs from each circular catheter acquisition was analyzed by the rotor detection method 50 in <1 second, which shows that the monitoring and detection of rotors can be done in real-time. Rotors were detected in 3 of 10 patients (median 2 per patient, range 1-2 per patient). The median number of rotations for these rotors was 2 (range 2-4) and the median periodicity CL covered by a single rotation was 91% (range 82-96%).

Figure 9:
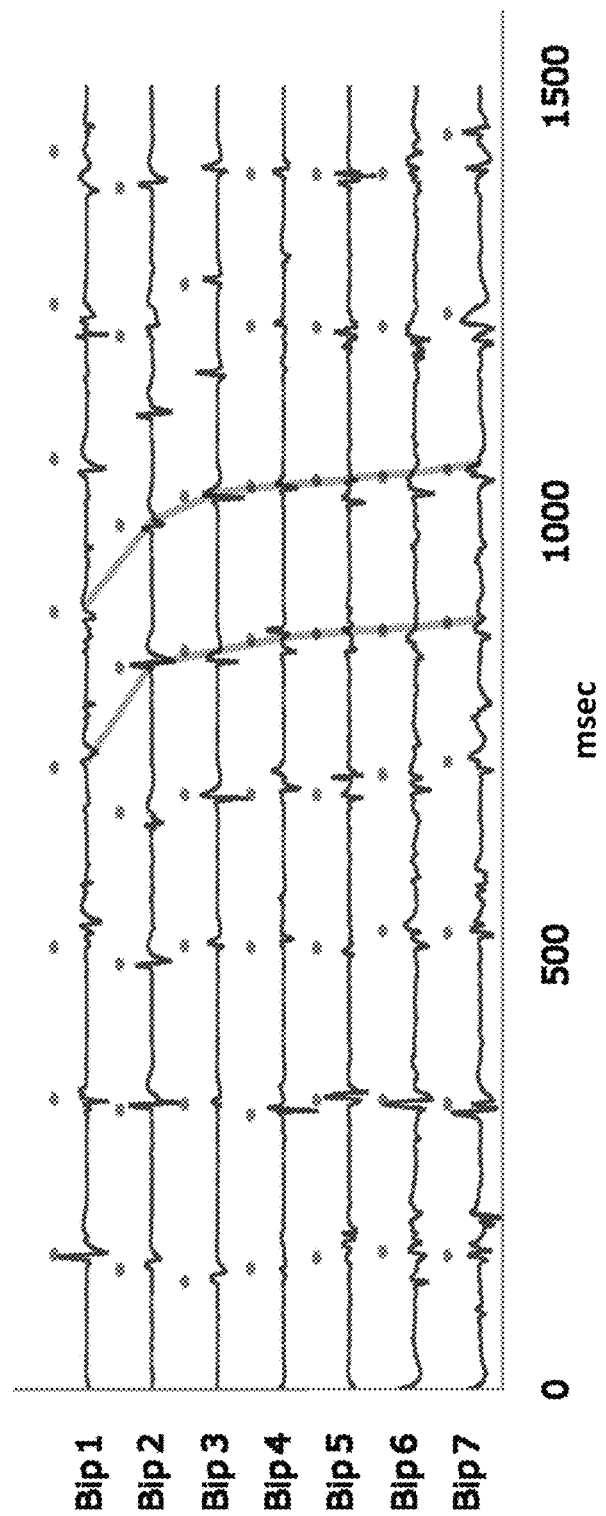
FIG. 9 shows an example of a rotor (as indicated by the slanting lines) detected from a sampled EGM dataset, containing 10 bipolar EGMs, in a patient with AF.

An example of a rotor detected in a patient is depicted in FIG. 9 which shows the bipolar EGM dataset that was recorded simultaneously from a 10-pole circular catheter in a patient with AF. The dots indicate periodic activations which were sustained for the 1500 ms duration of recording in each bipolar channel. The slanted line indicates a rotor detected automatically by the rotor detection method 50 based on the criteria described above. Two rotations are present from bipole 1 to 7. Other periodic activations are tracked by the rotor detection method 50 but do not fulfill criteria for a rotor.

As seen from Table I, the rotor detection method described in accordance with the teachings herein performs with high sensitivity in the presence of few confounding aperiodic peaks. However, as the number of aperiodic peaks increase, they can lie in proximity to periodic pulses, which can result in falsely detected periodic sequences. When these are identified as the dominant periodic sequences, false rotor tracking and detection may occur. As a result, the sensitivity of the rotor detection method decreases when the number of aperiodic peaks is very high. This is an important consideration since AF bipolar EGMs can be very complex with multiple aperiodic peaks. According to Table II, the number of rotations also influences the performance of the rotor detection method. If there are too few rotations, then the dominant frequency detection does not have enough data to robustly determine the correct dominant periodicity CL to be tracked. However, with at least 4 rotations, the sensitivity of the rotor detection method is high. This is clinically relevant as nonsustained rotors may be prevalent, which requires robust detection strategies. Unlike sensitivity, the specificity of the rotor detection method 50 remains high even with EGM datasets that simulate incomplete rotations. This attests to the stringency of the criteria to verify rotational activations and ensures that passive wave curvature is unlikely to be detected as a rotor. This is also clinically relevant as wave curvature is common in AF (see FIGS. 14 to 19B and the related clinical study below).

Figure 10:
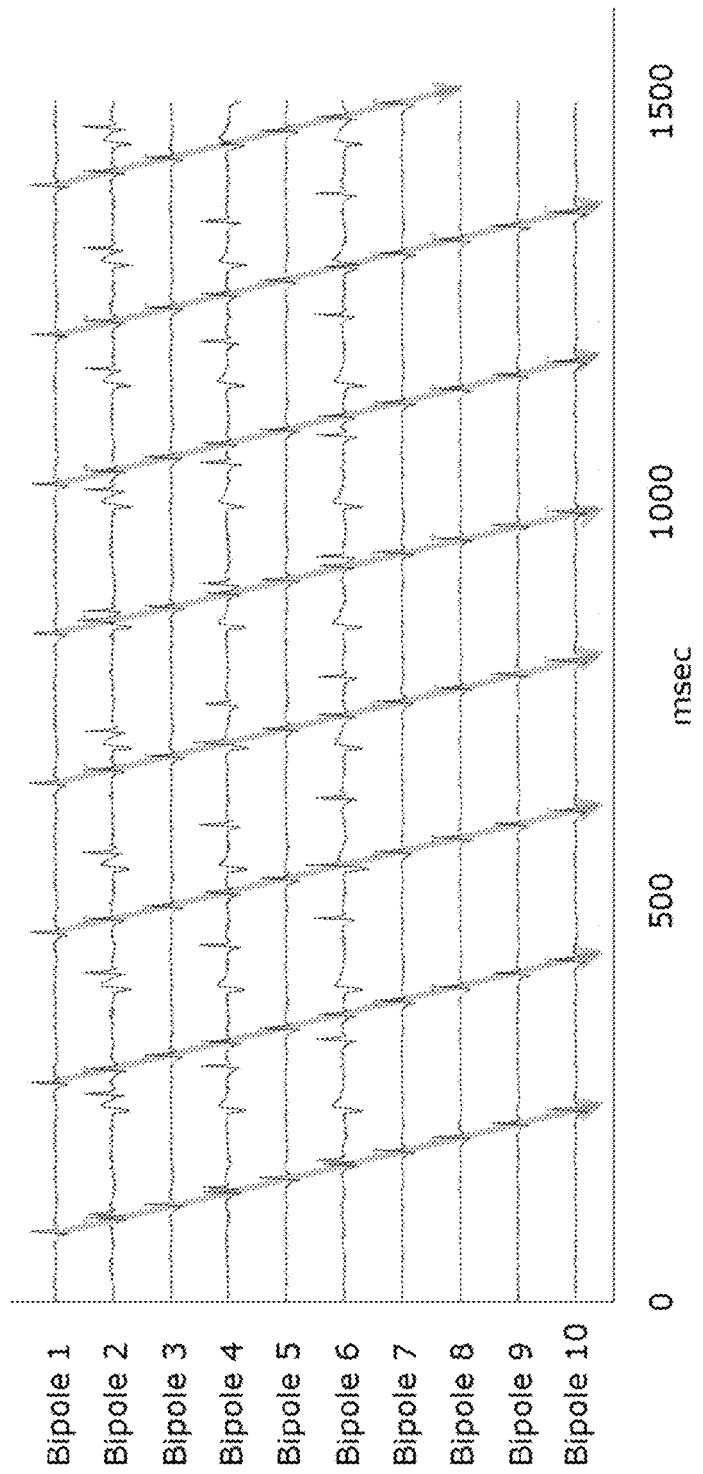
FIG. 10 shows a sampled EGM dataset, containing 10 bipolar EGMs, with synthetic AF signals and multiple periodic pulse trains, including the periodic pulse train of a rotor (periodicity cycle length: 186 msec) as shown by the slanting lines.

While periodic activations across multiple bipoles of a circular catheter may be tracked for the purpose of rotor detection, these periodic activations may be contaminated by other periodic pulse trains that originate remote from the rotor as shown in the example of FIG. 10. In particular FIG. 10 shows synthetic AF signals containing multiple periodic pulse trains including that of a rotor (periodicity CL: 186 msec). The downward slanting arrows indicate electrical impulse propagation of the rotor from bipole 1 to bipole 10 around the circular catheter. In bipoles 2, 4 and 6, there are two confounding periodic signals of higher frequency (periodicity CL: 145 msec and 154 msec) that are often larger in amplitude than the rotor's periodic signal of interest.

As described previously, most peak detection methods have focused on finding all valid peaks (after removing noise). In addition to the peak detection methods based on window-thresholding (Jacobson, 2001; Vivó-Truyols et al., 2005), K-Means clustering (Mehta et al., 2010), wavelet transform (Singh et al., 2011), and non-parametric approaches (Scholkmann et al., 2012; Ng et al., 2014), there are also methods based on linear prediction and higher-order statistics analysis (Lin et al.,1989; Panoulas et al., 2001), Empirical Mode Decomposition (Hadj et al., 2010), Hilbert transform (Benitez et al., 2001), and hidden Markov models (Coast et al., 1990).

However, many of these peak detection algorithms have 2 important limitations as previously described; i.e. they assume all valid peaks correspond to the periodic activity in the signal (for example, (Ng et al., 2014) use the annotated peaks to calculate the signal's periodicity)) and secondly they assume valid peaks are the largest local peaks. However, the inventors have found that in many real-world signals, neither assumption may be valid, as explained previously. These factors compromise the ability of these methods to find valid peaks corresponding to a periodic cycle length, even if there is only one periodic train in the signal. In addition, in the presence of multiple periodic trains, these methods will be further disadvantaged.

While the rotor detection method 50, described in accordance with the teachings herein, is designed to only detect peaks of a single dominant periodicity CL, in an alternative embodiment, the rotor detection method 50 is modified to identify individual periodic peak trains in signals containing multiple such periodic sequences having different dominant periodicity CL (Dalvi et al 2016b). Once each periodic pulse train is identified within a given bipolar EGM, the periodic pulse train corresponding to the rotor can be selected to improve the robustness of rotor detection amidst other periodic pulse trains that are not related to rotor activity. Dominant frequency-based periodicity detection along with a graph search methodology are still used to identify the most dominant periodic activation set or peaks of interest in this modified rotor detection method. However, in this alternative embodiment, the peaks of the dominant periodic activation set are removed and the method is iterated until all periodic sequences have been identified. The accuracy of this modified method to identify periodic peaks was evaluated on simulated AF intra-cardiac EGMs containing multiple periodic sequences of different frequency (i.e. periodic activation trains of three distinct frequencies) corrupted by noise and complex aperiodic signal features as described in further detail below.

Figure 11:
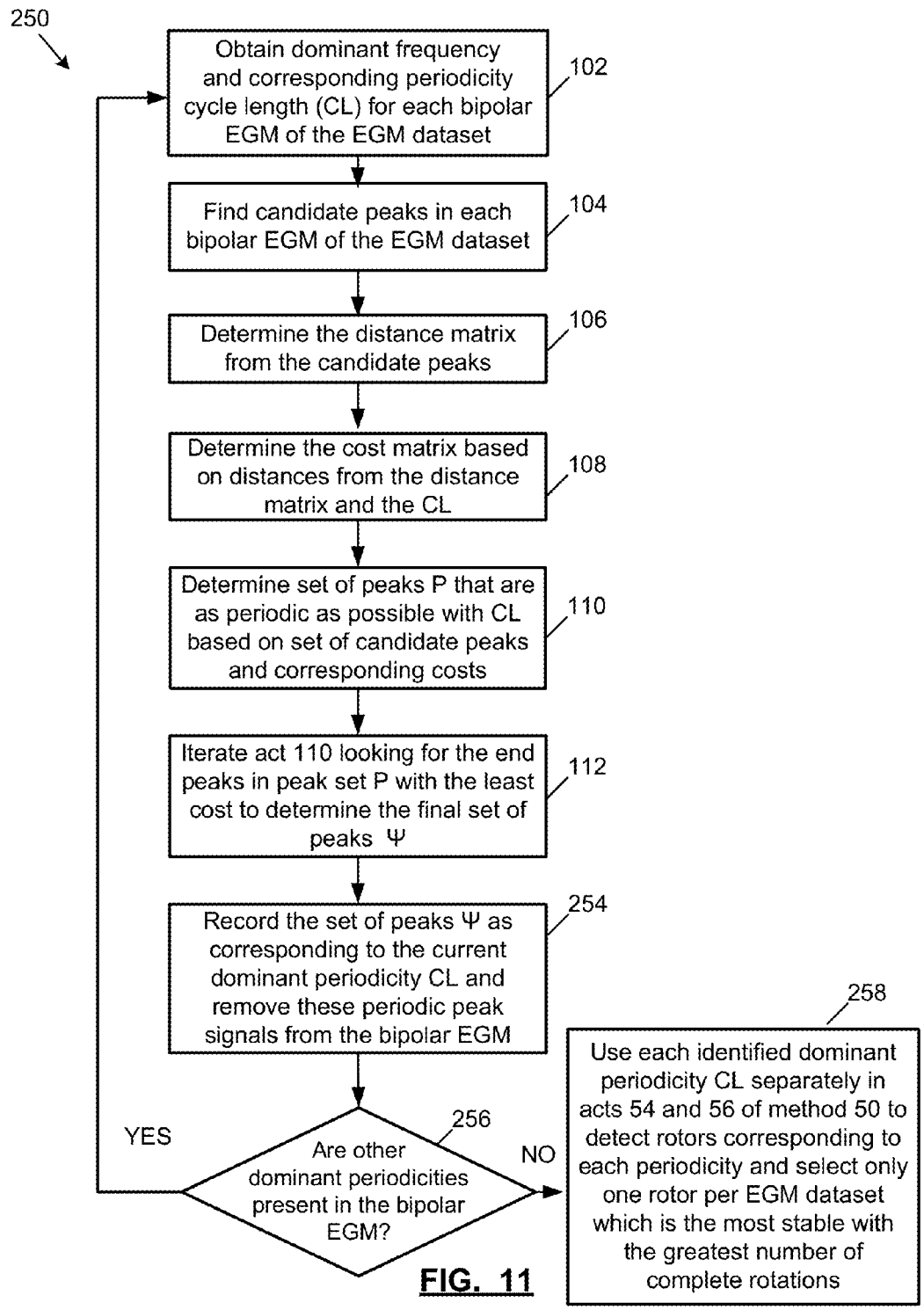
FIG. 11 is a flowchart of an example embodiment of a modified rotor detection method for detecting rotors where there are multiple periodicities in the bipolar EGMs of an EGM dataset.

The modified rotor detection method is similar to the rotor detection method 50 except for how the periodic activations are detected and selected from the bipoles of the circular catheter array. Referring now to FIG. 11, shown therein is a flowchart of an example embodiment of an alternate activation detection method 250 that may be used instead of the activation detection method 100 to detect periodic activations for the rotor detection method 50 for detecting rotors when there are multiple periodicities in the EGM dataset.

Acts 102, 104, 106, 108, 110 and 112 are repeated for the alternate activation detection method 250.

The method 250 then proceeds to act 254 where the set of peaks Ψ is stored as the peaks that correspond to the current dominant periodicity CL. These periodic peak signals are blanked or removed from each bipolar EGM of the EGM dataset using a blanking window of width b on either side of the identified peaks in the set of peaks Ψ. The blanking window width is typically set to 50-75 msec to correspond to the absolute cardiac refractory period.

The method 250 then proceeds to act 256 at which point it is determined if there are other dominant periodicities in the residual bipolar EGM. If this determination is true, then the method 250 proceeds to act 102 and performs acts 102-112 and 254-256 repeatedly until no further dominant periodicities are detected. Additional dominant periodicity is present if, for example, the spectral power of the DF in the residual bipolar EGM is greater than a power spectral threshold of the entire spectral power of the residual bipolar EGM (i.e. the power of its PSD). The power spectral threshold may be set to 10-15%, for example as defined previously.

When the determination at act 256 is false and there are no other dominant periodicities in the bipolar EGMs of the EGM dataset, the method 250 proceeds to act 258 and stops. At this point, each dominant periodicity CL identified by method 250 is used separately in acts 54, and 56 of the rotor detection method 50 to detect potentially more than one rotor, each having one of the identified dominant periodicity CLs. For a given EGM dataset recorded from a circular electrode array, which has multiple dominant periodicities, only one rotor is selected since physiologically there can only be one rotor at a given recording location in the heart. The rotor that is selected is the one with the greatest number of complete rotations, since this rotor is considered to be the most stable based on experimental data.

Validation Using Simulated Periodic Signals and Comparator Methods

Figure 12:
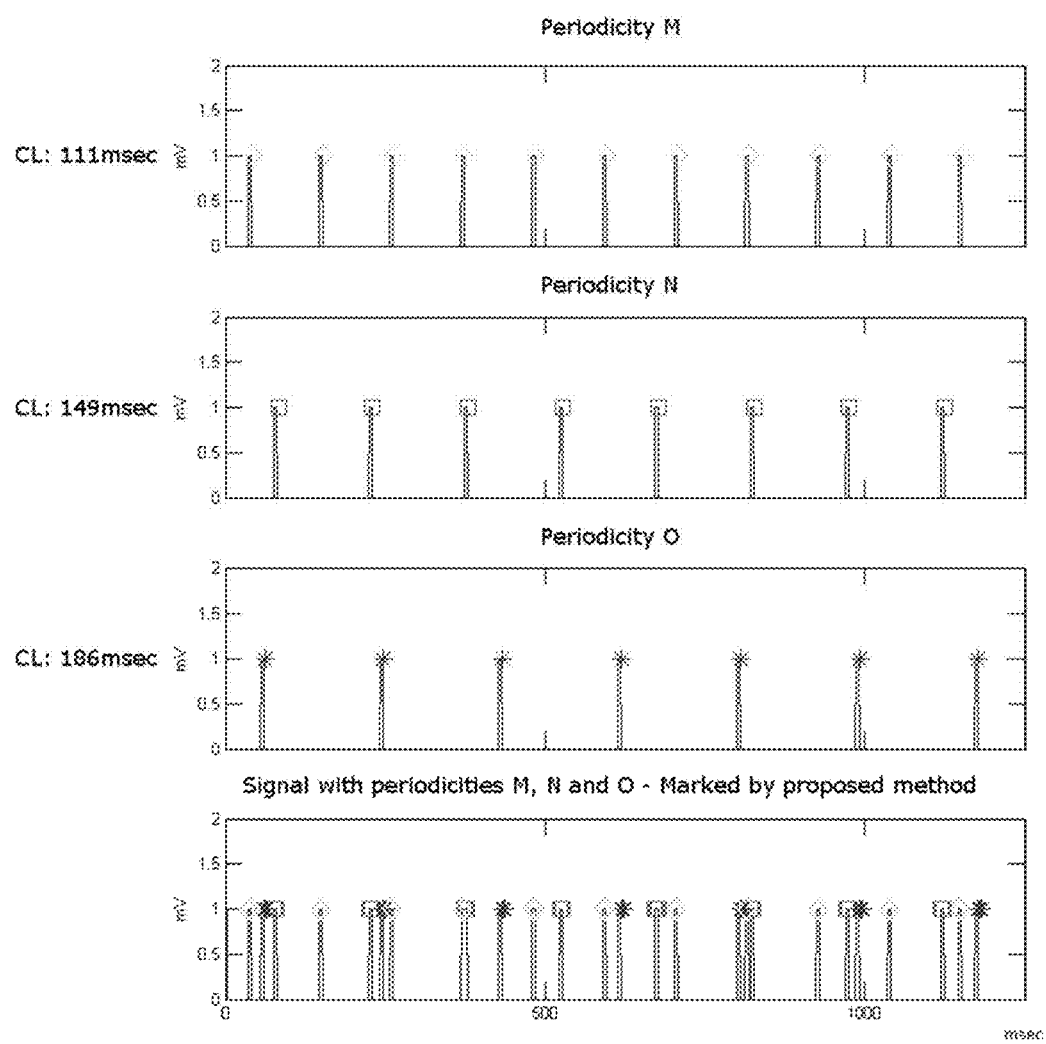
FIG. 12 shows three simulated periodic signals each with different periodicity cycle lengths (as shown in 3 different bipolar EGMs) and the results of the modified rotor detection method being applied to detect the periodic peaks of interest for each of these 3 periodic signals and the combination of the 3 different simulated periodic signals.

Referring now to FIG. 12, shown therein are three simulated periodic signals (M, N, O) with different periodicity CL and the results of the modified rotor detection method being applied to the combination of the three simulated periodic signals. The bottom panel in FIG. 12 combines the three simulated signals. The periodic peaks identified by the modified rotor detection method are shown by diamonds, squares, and asterisks. Each periodic peak is assigned correctly to its periodic pulse train of origin.

The performance of the modified rotor detection method was compared with a contemporary algorithm for peak localization (Ng et al, 2014). Briefly, Ng et al. have proposed a cycle length iterative (CLI) method that iteratively alters the cut-off threshold for peak detection and calculates the mean and median CL at each iteration. The CLI method terminates when the mean and median converge, and the cut-off threshold obtained is used to detect peak activations.

To test the performance of the modified rotor detection method, 750 different synthetic AF signals were generated, each having a 2.5 second duration. Each AF signal contained the sum of three pulse trains having distinct periodicities (the periodicity CL was between 105 and 195 msec). Each pulse train was constructed from a template bipolar EGM recorded in the left atrium of a patient with AF. The periodic pulse trains had pulses of varying amplitude. The AF signal was also contaminated by white noise and aperiodic pulses of varying amplitude.

In order to evaluate the performance of the modified rotor detection method in detecting periodic peaks in the 750 synthetic AF signals, each extracted pulse train's annotated peaks were compared to the location of known periodic peaks for that pulse train. If the known peak location and the annotated peak location were within 10 msec of one another, the annotation was considered accurate. The performance of the modified rotor detection method in detecting the correct periodic peaks from a particular pulse train was described in terms of specificity (true negative/(true negative+false positive)) and sensitivity (true positive/(true positive+false negative).

The performance of the modified rotor detection method and the CLI method is summarized in Tables III and IV. Each table presents the sensitivity and specificity for a single periodic pulse train, as a control, and multiple periodic pulse trains (i.e. 3 trains). Both single and multiple periodic pulse trains are contaminated with aperiodic pulses of varying amplitude. The performance of the two methods in increased white noise is also shown.

TABLE III

Sensitivity of Tested Methods in detecting periodic pulse train

| Sensitivity (%) | | | | |
| --- | --- | --- | --- | --- |
| Single Periodic Pulse Train + | SNR (dB) | | | |
| Aperiodic Pulses | -3 | 0 | 3 | 5 |
| CLI Method | 76 | 83 | 93 | 95 |
| Modified Rotor Detection Method | 86 | 93 | 100 | 100 |

| Sensitivity (%) | | | | |
| --- | --- | --- | --- | --- |
| Multiple Periodic Pulse Trains + | SNR (dB) | | | |
| Aperiodic Pulses | -3 | 0 | 3 | 5 |
| CLI Method | 83 | 85 | 90 | 92 |
| Modified Rotor Detection Method | 85 | 89 | 98 | 98 |

TABLE IV

Specificity of Tested Methods in detecting periodic pulse train

| Specificity (%) | | | | |
| --- | --- | --- | --- | --- |
| Single Periodic Pulse Train + | SNR (dB) | | | |
| Aperiodic Pulses | -3 | 0 | 3 | 5 |
| CLI Method | 79 | 85 | 88 | 91 |
| Modified Rotor Detection Method | 88 | 95 | 100 | 100 |

| Specificity (%) | | | | |
| --- | --- | --- | --- | --- |
| Multiple Periodic Pulse Trains + | SNR (dB) | | | |
| Aperiodic Pulses | -3 | 0 | 3 | 5 |
| CLI Method | 14 | 17 | 17 | 19 |
| Modified Rotor Detection Method | 86 | 91 | 95 | 98 |

Figure 13:
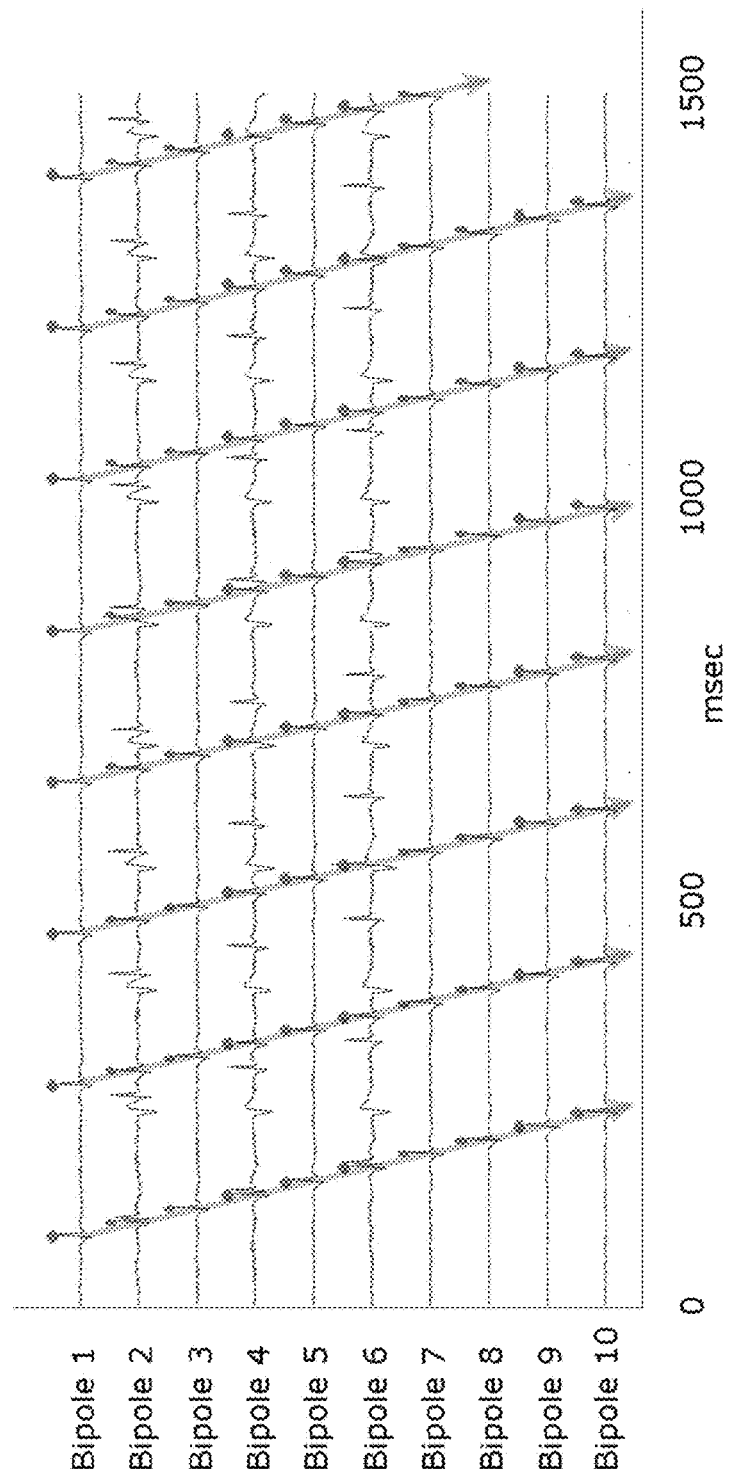
FIG. 13 shows synthetic AF signals containing multiple periodic pulse trains including the periodic pulse train of a rotor that is tracked across the EGM dataset as shown by the slanting lines (asterisks indicate periodic activations).

For illustrative purposes, FIG. 13 demonstrates periodic peak annotations corresponding to the periodicity of interest, that being the periodicity of a rotor as shown in FIG. 10. In particular, FIG. 13 shows synthetic AF signals containing multiple periodic pulse trains including that of a rotor. The periodic peaks of the rotor progress temporally from bipole 1 to 10 as depicted in FIG. 10. In order to identify the rotor, the periodicity of interest was chosen to be the one which is dominant in all 10 bipoles of the circular catheter. The asterisks are the periodic peaks annotated by the modified rotor detection method, based on the rotor's dominant periodicity CL of interest. As can be seen, the modified rotor detection method accurately identifies all peaks of the rotor's pulse train, even in the presence of other periodic peaks with higher frequency, which are often larger in amplitude than the rotor peaks. Also, the periodic pulse train in each bipole is identified independently of the periodic pulse train in the other bipoles.

The modified rotor detection method maintains high sensitivity and specificity in detecting periodic peaks of a particular periodicity CL in synthetic AF signals with multiple periodic pulse trains. The modified rotor detection method is shown to have high accuracy (up to 100% sensitivity and 100% specificity) in detecting the three individual periodic peak trains. The sensitivity and specificity is slightly lower when the modified rotor detection method is applied to AF signals with multiple periodic pulse trains compared to those with a single periodic pulse train. However, the performance remains robust even in the presence of varying periodic peak amplitude, contaminating aperiodic peaks, and noise. In contrast, the CLI method has significantly lower specificity when applied to signals with multiple periodicities due to its tendency to detect peaks based on amplitude rather than periodicity CL. Consequently, the CLI method detects all valid peaks, even some aperiodic peaks, and does not specifically identify which periodic pulse train the peaks belong to.

It should be noted that the modified rotor detection method is designed using a few assumptions: 1) the signal contains periodic pulse trains, and 2) the peaks belonging to those pulse trains are the only peaks of interest. Hence, one anticipates that the modified rotor detection method will outperform the CLI method which annotates any peak that meets validity criteria for general peaks without any attempt to detect periodic peaks in the EGM. This is precisely what the majority of peak detection algorithms are designed for. Therefore, their performance on complex signals with multiple periodic pulse trains and aperiodic peaks will be poor, when the objective is to extract peaks specifically corresponding to periodic pulse trains.

Large Prospective Study in Patients with Atrial fibrillation

Based on animal and computational studies (Nattel, 2002), periodic rotational electrical activity (a.k.a. rotor or re-entry) in the human atrium can drive atrial fibrillation (AF). These rotors often anchor to myopathic or scarred regions in the atrium and their ablation can terminate AF in animal models (Heijman et al., 2016). Repetitive and periodic activation of stable cycle length (CL) is inherent to cyclical rotational activity along the path of rotation of these rotors (Vijayakumar et al., 2016; Lee et al., 2017). It has recently been shown that sustained periodic electrical activity of 5 seconds duration is common in endocardial AF bipolar electrograms (EGM) in patients presenting for catheter ablation (Gizuzarson et al., 2016). Such periodicity can vary widely in location in the LA and PV. However, detection of rotational activation in human AF is challenging owing to the inherently complex signal features.

This study evaluated the prevalence and stability of rotational activity (RO) and wave curvature (WC) at sites with periodic activity in LA in patients with AF undergoing catheter ablation. An alternative embodiment of an automated periodicity detection and tracking method in accordance with the teachings herein was used in this study. This approach provides an unbiased, objective interpretation of propagation, which to date has been achieved ad hoc with visual inspection alone. Another potential advantage of automating the detection of rotation is the ability to distinguish it from pseudo-rotation or wave curvature, where the rotation is incomplete or there is one rotation, and cases where the rotation is not sustained. Pseudo-rotation is not an AF driver, but instead represents passive wave curvature. A secondary objective was to determine the spatial relationship of RO and WC to atrial myopathy which may be defined by voltage mapping.

In order to distinguish transient Rotational Activation, which may be less impactful as a putative AF driver, the automated analysis for the study was adjusted to select stable RO patterns by analyzing only sites with sustained periodic activity lasting 5 seconds. The periodic activations recorded from each bipole of the circular catheter were tracked temporally to assess propagation, as either (i) wave curvature (i.e. sequential activation with similar periodicity on the entire circular catheter covering <80% of periodicity CL for ≥2 cycles), or (ii) rotational activity (i.e. sequential activation with similar periodicity on the entire circular catheter covering ≥80%, of periodicity CL for ≥2 cycles). It should be noted that this particular definition of WC was used in this clinical study to be more stringent and improve specificity of WC detection. Furthermore, this particular definition of rotational activity also applies to rotor detection, but for the purpose of this clinical study, the term rotational activity is used rather than rotor.

The study was performed on 70 patients (age 61±10 years, paroxysmal=63%) undergoing their first catheter ablation procedure for symptomatic drug refractory high burden paroxysmal AF or persistent AF. Patients with prior ablation for AF and those with severe valvular heart disease or cardiomyopathy were excluded. The study was approved by the University Health Network Research Ethics Board and all patients provided written informed research consent.

High-density endocardial LA and PV activation mapping was performed during AF in all patients. In patients presenting in sinus rhythm, AF was induced using burst atrial pacing at a CL of 180-250 ms from a coronary sinus electrode and if necessary, isoprenaline infusion (1-4 µg/min). EGMs were acquired only when AF was sustained for more than 5 minutes, after which rotor analysis was performed.

A roving 20-pole circular catheter (Lasso® Nav Variable, 25-15 mm diameter, 1 mm electrodes at 2-6-2 mm spacing, Biosense Webster, Diamond Bar, Calif.) introduced through a transeptal access was used for endocardial LA mapping. Electroanatomic mapping was performed on the CARTO® 3 (Biosense Webster, Diamond Bar, Calif.) system, guided by a pre-operative contrast CT reconstruction of the LA and PV anatomy. At each location, the circular catheter was shaped to its 15 mm diameter whenever possible. Stable tissue contact and signal quality was ensured before EGM acquisition. A set of 7 simultaneously recorded bipolar (30-500 Hz) EGMs of 5 second duration was then obtained at each anatomic location. Mapping was targeted to all locations in the LA and PVs, aiming for a uniform density of points across regions whenever possible. Electroanatomic data was exported for off-line analysis using custom software developed in MATLAB (Mathworks Inc., Natick, Mass.).

A baseline high density LA bipolar voltage map in sinus rhythm was also acquired at the discretion of the operator of the study. Bipolar EGMs with peak-to-peak voltage <0.5 and ≥0.5 mV were regarded as low and normal voltage, respectively (Lim et al., 2014). An activation pattern during AF was considered concordant to a low voltage zone if within a distance of <10 mm.

All statistical analyses were performed using SPSS software version 17.0 (SPSS, Chicago, Ill., USA). Continuous variables are reported as mean±standard deviation or median, as appropriate. Categorical variables are reported as numbers and percentages. All tests were two-sided and a p-value<0.05 was considered statistically significant.

Figure 14:
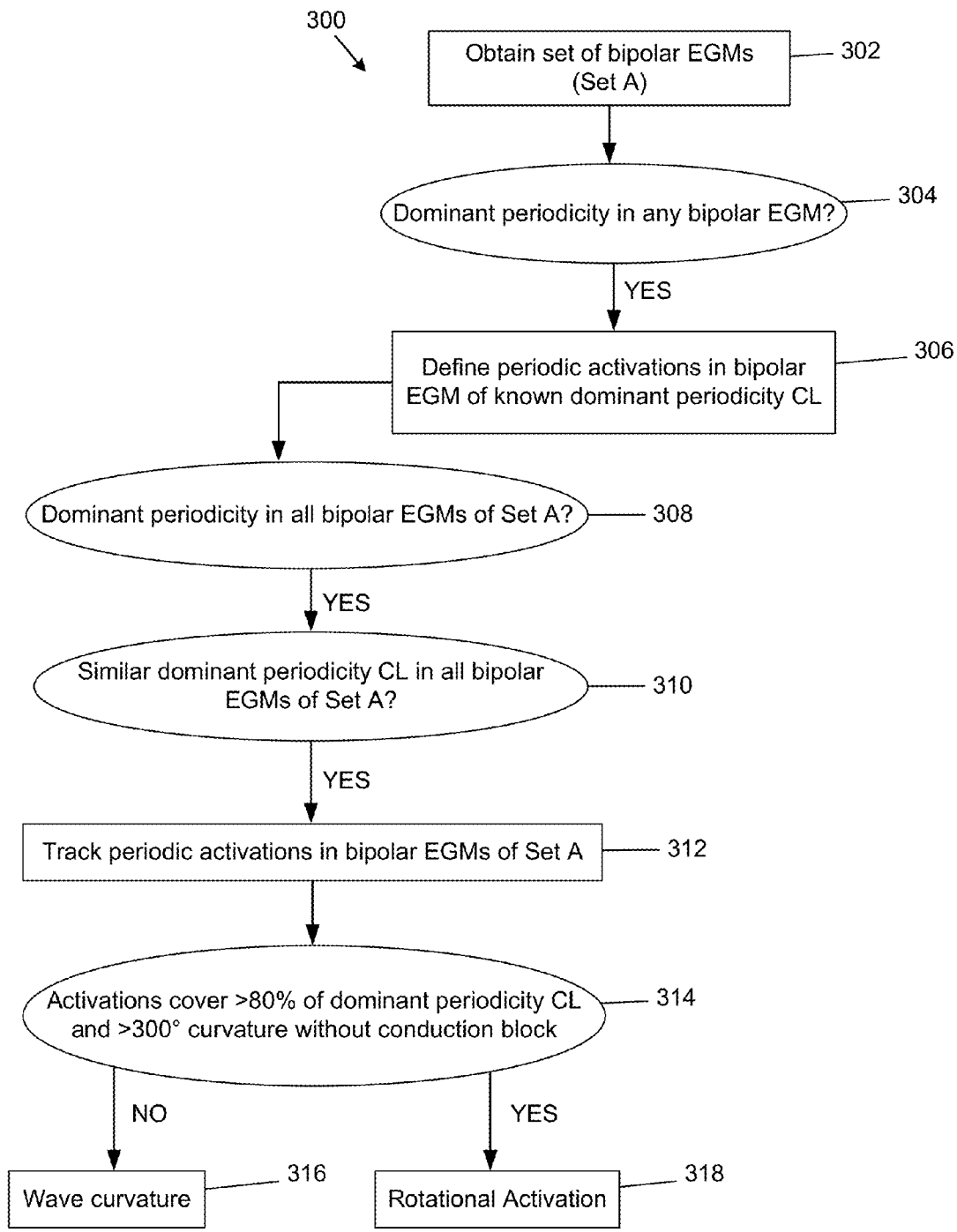
FIG. 14 is a flowchart of another example embodiment of a rotor detection method for distinguishing rotational activation from wave curvature in cardiac fibrillation.

Referring now to FIG. 14, shown therein is a flowchart of an example of an alternative embodiment of a periodic activation detection and tracking method 300 that was used for this study for distinguishing rotational activation from wave curvature in cardiac fibrillation. The method 300 is similar to methods 50 and 100 with some slight differences compared to the periodic activation tracking method 150 and the rotational activation sorting method 200. The method 300 can be used for tracking periodic activations in bipolar EGMs in order to determine whether there is rotational activation or wave curvature.

At act 302, a set of 7 bipolar EGMs (i.e. Set A) was acquired for 5 seconds at each circular catheter location and preprocessed as described above. In other embodiments, a different number of sets of bipolar EGMs can be acquired for a different duration of time.

At act 304, the bipolar EGMs with dominant periodicity were determined in a similar fashion as acts 52, 102 and 152 of methods 50, 100 and 152, where dominant periodicity is defined as the inverse frequency encompassing at least 10% of the spectral power. A threshold other than 10% can be used in other embodiments. However, act 304 of method 300 was modified such that it is possible to exclude certain sites where the dominant periodicity is too large (i.e. a dominant periodicity having an amplitude that is larger than a dominant periodicity threshold), such as sites with a dominant periodicity CL>250 ms for example, as such a CL is too slow to function as an AF driver. In other embodiments another dominant periodicity threshold may be used such as 50 to 250 ms, for example, based on animal studies evaluating rotor periodicity CL.

If dominant periodicity was found in any bipolar EGM, then at act 306 the periodic activations of known periodicity CL are defined using a graph-search based periodic peak detection model, as defined previously in acts 104 to 112 of method 100.

At acts 308 and 310, if the dominant periodicity was found in all bipolar EGMs of Set A and if similar dominant periodicity CL were found in all bipolar EGMs of Set A, then the method 300 proceeds to act 312 and periodic activations were tracked. Acts 308 and 310 are generally the same as acts 152 to 162 of method 150 with a few modifications in selecting and finding the rotor activation candidates that correspond to one rotation as was defined in acts 160 and 162. Act 310 comprises performing the modified version of acts 160 and 162 to find candidate rotational activations, which is similar to finding rotor activation candidates but is done using stricter criteria for this clinical study to further distinguish from wave curvature.

In act 310, the modified version of act 160 comprises locating the first activation (across all bipoles) and labelling it as a member of a candidate rotation n (n=1 for the first candidate rotational activation). It is considered the current activation (CA). The other activations that belong to the candidate rotation are then located starting with the nearest periodic activation that is not yet assigned to a candidate rotation in the subsequent bipolar EGMs which is either in the bipole that is before or after the bipole having the CA, and within one dominant periodicity CL of the CA. This corresponds to clockwise rotational activation in the circular electrode array as per the example shown in FIG. 2. For anticlockwise rotational activation, the searching for other candidate rotations after the identification of the CA can be reversed. This searching may first be checked assuming clockwise rotational activation and if no candidate rotational activations are found, the searching may then be done assuming counter-clockwise rotational activation.

If an activation (A) which is after, and within, one dominant periodicity CL of the CA is found, then the located activation is added to candidate rotational activation n. This located activation is now considered to be the CA and the searching defined in the previous paragraph is repeated. If no valid activation is found and all activations in the EGM dataset have not yet been assigned to a candidate rotational activation or the activation (A') is before the CA, then n is adjusted according to n=n+1 and searching begins for a new candidate rotational activation. Activation A' (if it is found) or the earliest activation not yet assigned to a candidate rotational activation is then searched for and set to the current candidate rotational activation and then candidates for the neighboring bipolar EGMs are searched for as described above. If the final activation in the EGM dataset has been reached, then act 310 comprises proceeding with a slightly refined and alternative version of act 162.

Act 310 now includes performing a slightly refined and alternative version of act 162. A running window of width equal to periodicity CL is slid across each candidate rotational activation found previously. A count of the number of times (represented by rt) that the running window transitions from (a) having the number of activations belonging to the candidate rotational activation being greater than the rotor activation candidate threshold (e.g. 0.7 for 7 bipoles) multiplied by the number of bipoles (i.e. number of channels or EGM datasets) to (b) the number of activations belonging to the candidate rotational activation being less than the rotor activation candidate threshold multiplied by the number of bipoles is performed. In this embodiment, a different threshold is used for the rotor activation candidate threshold. The first activation in the running window every time it transitions from (b) to (a) is considered the start of a new candidate rotational activation and the original candidate rotational activation is split accordingly. Furthermore, activations that never featured in the running window while in phase (a) above are dropped.

The aforementioned rotor activation candidate threshold may be set in various ways. For example, the rotor activation candidate threshold may be at least (n/2)+1 or ((n+1)/2)+1 (depending on whether n (i.e. the number of bipoles) is even or odd) of the total number of bipole channels (i.e. total number of EGM datasets). This threshold represents the minimum number of distinct electrodes that have activations that form the candidate rotational activation to ensure that the staggered activation pattern along the circular catheter electrode array indicates rotational activation and not planar activation. Alternatively, a more stringent threshold might be used such as n−1 out of n bipoles as was done in this study where this particular threshold was set to be 6 out of 7 bipoles.

At act 312, among the circular catheter acquisitions with 7 bipolar EGMs demonstrating similar dominant periodicity CL (e.g. ±10% of the median periodicity CL of 7 bipoles in method 300 although this range can be varied in alternative embodiments), the periodic activations are tracked across adjacent bipoles to determine whether their path conforms temporally to rotational activation, either clockwise or counter-clockwise, and span the periodicity CL without conduction block. Accordingly, method 300 includes the additional step of determining the presence or absence of local conduction block during a candidate rotational activation (e.g. see FIGS. 15A and 15B).

FIG. 15A shows the result of periodicity peak detection in 5 bipolar EGM recordings during AF in a patient. For each bipole, periodic peaks (i.e. activations) are correctly detected (see dashed line) regardless of their amplitude, while larger aperiodic peaks are ignored. The periodicity CL is similar for all 5 bipolar EGMs. FIG. 15B shows the result of tracking these periodic peaks across adjacent bipoles (see dotted lines). Rotational activation is detected in FIG. 15B which spans the periodicity CL of the constituent bipoles. Local conduction block is presumed when the activation time difference between two adjacent bipoles on the circular catheter is >50 ms (i.e. conduction velocity <0.12 m/s) (Lee et al., 2014).

In this example embodiment of the method 300, local conduction block was presumed when the activation time difference between two adjacent bipoles on the circular catheter was greater than a time threshold which corresponds to a conduction velocity threshold. In this example embodiment, the time threshold was set to be >50 ms, which corresponds to a conduction velocity <0.12 m/s) (Lee et al., 2014) based on the fixed distance between recording bipoles on the circular catheter. If local conduction block is present, then rotational activation was considered to not be due to a rotor. Checking for conduction block is not done in conventional rotor detection.

The method 300 then proceeds to act 314 which includes determining whether certain threshold criteria are satisfied for classifying the tracked periodic activations obtained using the circular catheter electrode array as either being a rotational activation or wave curvature. In this example embodiment, if the number of activations having a similar dominant periodicity CL (e.g. within 5 to 10% variation) is greater than a periodic activation detection threshold of the total number of activations (similar to act 156) and if the activations cover a curvature threshold without conduction block, then the activations are classified as a rotational activation (RO) and the method 300 proceeds to act 318 to verify whether it is a rotational activation. In this example embodiment, the periodic activation detection threshold can be 80% and the curvature threshold can be 300° of curvature. In alternative embodiments, the periodic activation detection threshold can vary between 70 to 80% and the curvature threshold can vary from 270° to 360° of curvature. However, if neither of these criteria are met, then the activations might be a wave curvature and the method 300 proceeds to act 316 to verify whether the activations are part of a wave curvature. Using the curvature threshold reduces the possibility of a planar activation being classified as a rotational activation when using a circular catheter electrode array with 10 recording bipoles.

At act 316, the activations are defined as a wave curvature when the set A of bipolar EGMs from the circular catheter recording have a similar periodicity CL and a sequential activation arising from a minimum number of bipoles (i.e. rotor activation candidate threshold which is 6 of 7 in this example embodiment) and does not cover the periodic activation duration threshold (which is <80% of the median dominant periodicity CL of the bipoles in this example embodiment) and does not cover the curvature threshold (which means it is <300 degree in this example embodiment) for more than a cycle threshold (which is ≥2 cycles in this example embodiment) during the recording window (which is 5 seconds in this example embodiment).

If a line of conduction block was present between two of the component bipoles of a wave curvature, it was considered a complex occurrence when the sequential wave curvature activation was made up by either detoured conduction between the two bipoles or invasion of another asynchronous wavefront of similar periodicity beyond the line of conduction block. For wave curvature occurrences of the complex type, only the number of circular catheter bipoles without an intervening line of block was reported.

At act 318 the activations are defined as a rotational activation when the set A of bipolar EGMs have a similar periodicity CL and a sequential activation arising from a minimum number of bipoles (i.e. rotor activation candidate threshold which is 6 of 7 in this example embodiment) and covers more than the periodic activation duration threshold (which is >80% of the median dominant periodicity CL of the bipoles in this example embodiment) and covers more than the curvature threshold (which is >300 degrees in this example embodiment) for more than a cycle threshold (which is ≥2 cycles in this example embodiment) during the recording window (which is 5 seconds in this example embodiment) (Dalvi et al., 2016a).

Results

Patient Demographics

The Baseline characteristics are presented in Table V. Seventy patients were studied (paroxysmal=63%, persistent=37%) and their LA diameter was 41±6 mm. All patients had preserved left ventricular ejection fraction. At the time of the mapping procedure, 76% of patients were taking an antiarrhythmic medication.

Mapping Details

At the commencement of the study, 28 (40%) patients were in AF, while AF was induced in 42 (60%) patients, of which 16 (23%) required isoprenaline. The LA sampling density in all patients was >450 points. Mean AF CL was 189±36 ms in the LA appendage. Sites with periodic activation were observed in 100% of patients, and more ubiquitous in induced than spontaneous AF. Sixteen patients also underwent LA bipolar voltage mapping in sinus rhythm.

Wave curvature

Seven (10%) of the 70 patients had a WC pattern transiently appearing on one of their circular catheter recordings. The demographic profile of these patients was comparable to the rest of the cohort (see Table V). However, mean AF CL in the LA appendage was shorter by 32 ms in patients with WC or a RO pattern than the rest of the cohort (162±19 vs. 193±36 ms, p=0.02). Details of the WC locations are presented in Table VI. The WC mean CL was 170±11 ms, and lasted for 3±0.9 cycles. At these locations, 41±23% of the periodicity CL was covered by the WC over the circular catheter bipoles.

Figure 16A:
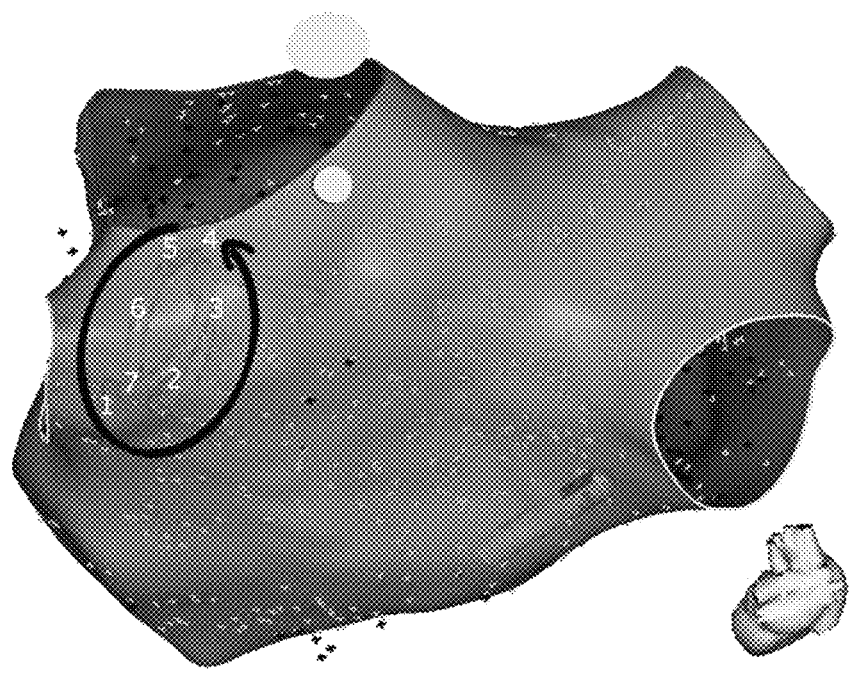
FIG. 16A shows an example of a circular catheter recording set near a left lower pulmonary vein (PV) on a left atrium, with arrows marking the chirality of propagation for patient #50 in the study.
Figure 16B:
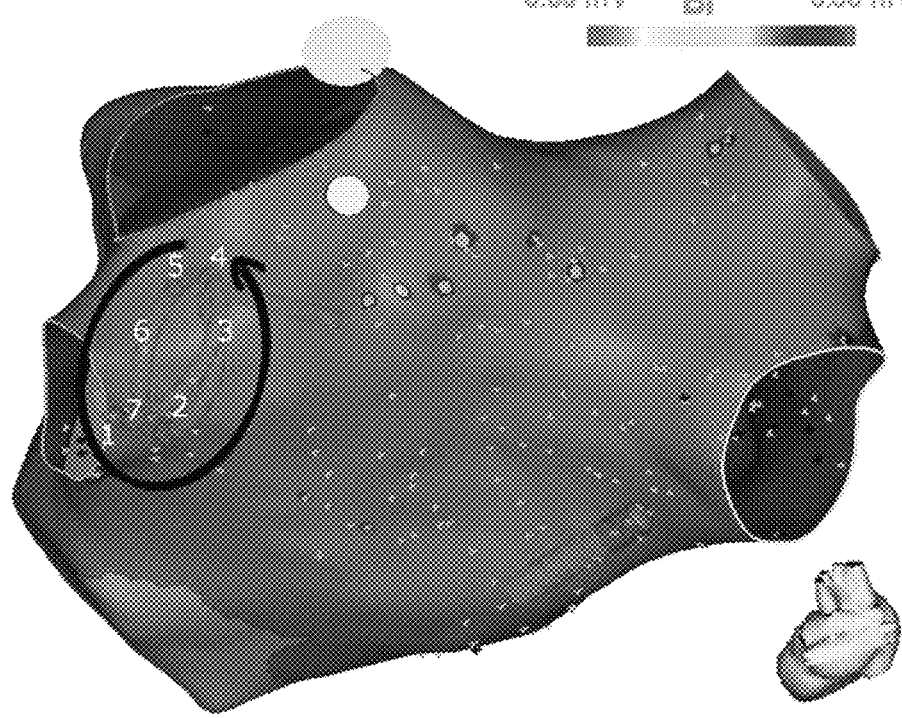
FIG. 16B shows an example of a left atrial voltage map based on the same heart and the same view as shown in FIG. 16A.
Figure 16C:
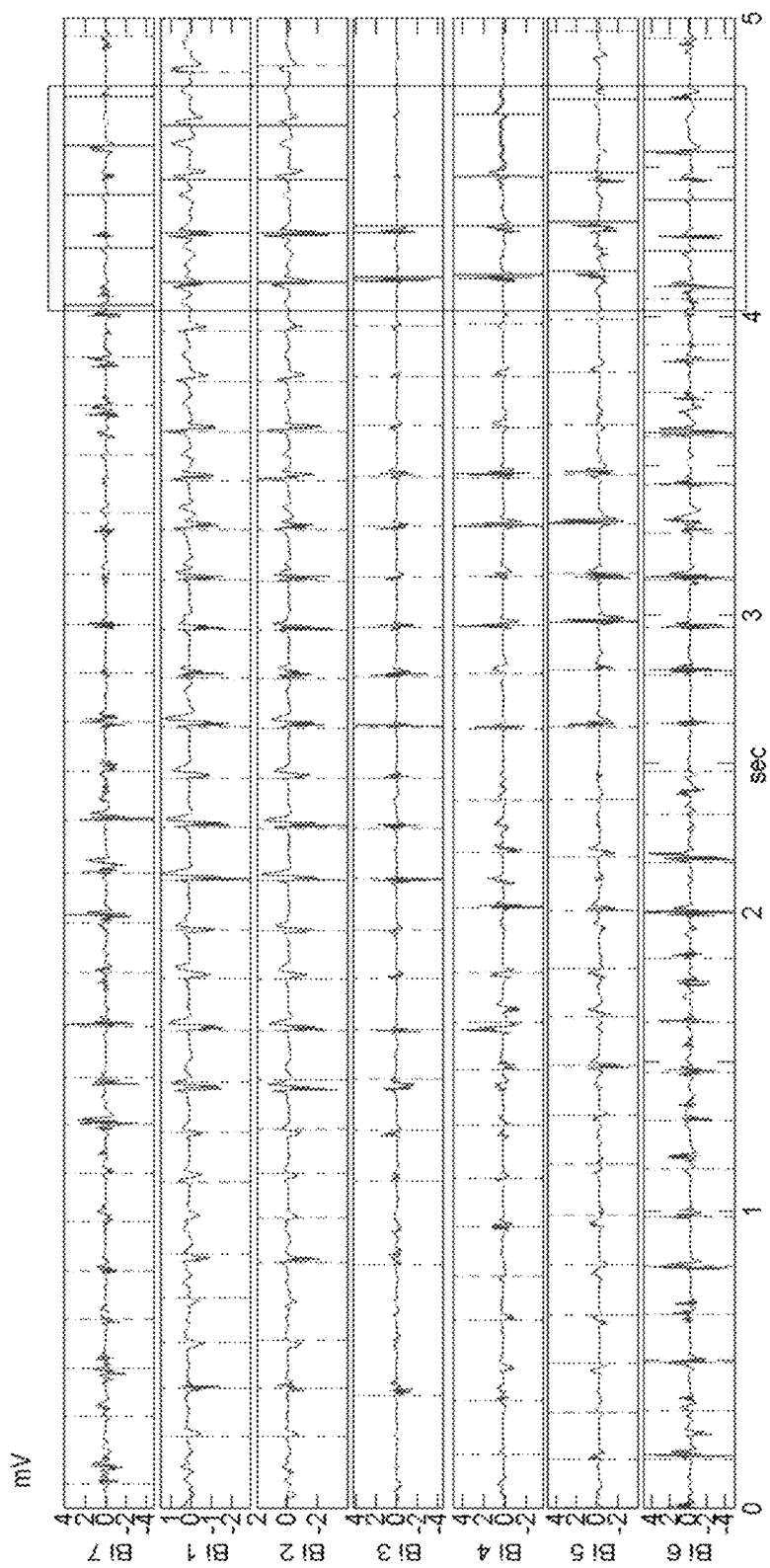
FIG. 16C shows an example of bipolar EGMs obtained over a 5 second duration from the circular catheter location in FIG. 16A.

FIG. 16C illustrates the solitary WC pattern seen in patient #50 in the study near the left lower PV on the posterior LA wall. During the last-third of this 5-second recording, the activation organizes to a WC pattern transiently for 5 cycles, when 50% of the prevailing periodicity CL is covered over 6 bipoles. In FIG. 16A, a posterior-anterior view of the left atrium is shown with a circular catheter recording set (1-7 bipoles) located on the posterior wall near the left lower PV. FIG. 16B shows a left atrial voltage map of the same heart based on the same view. There are no significant areas of low voltage on the posterior wall. The arrows in FIGS. 16A and 16B mark the chirality of propagation. FIG. 16C shows bipolar (1-7) electrograms obtained over a 5-second duration from the circular catheter location in FIG. 16A. All 7-bipoles had a stable periodic CL of 172 ms. Periodic activations at each bipole are marked by broken vertical lines. The activation organizes itself to a wave curvature pattern between 4.1 and 4.7 seconds of the recording (see the boxed area in FIG. 16C). As there is an activation time difference of >50 ms between adjacent bipoles 6 and 5 in the clockwise direction, it's likely that activation from bipole 6 blocked clockwise towards bipole 5, but proceeded in a counterclockwise direction in a winding course to bipole 5. This is evident by sequential activations (marked by vertical lines) along the circular catheter in a counterclockwise direction for 5 cycles covering 50% of the 172 ms periodicity CL in each of the first 4 cycles.

Figure 17A:
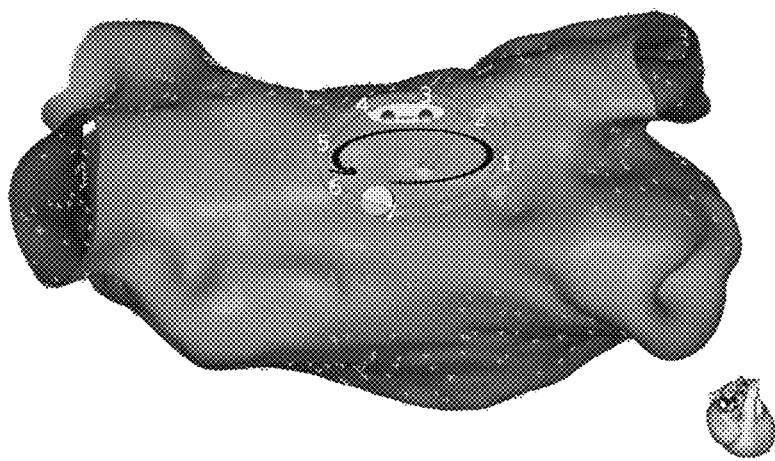
FIG. 17A shows an example of a circular catheter recording set on a posterior wall of a left atrium, with arrows marking the chirality of propagation for patient #24 in the study.
Figure 17B:
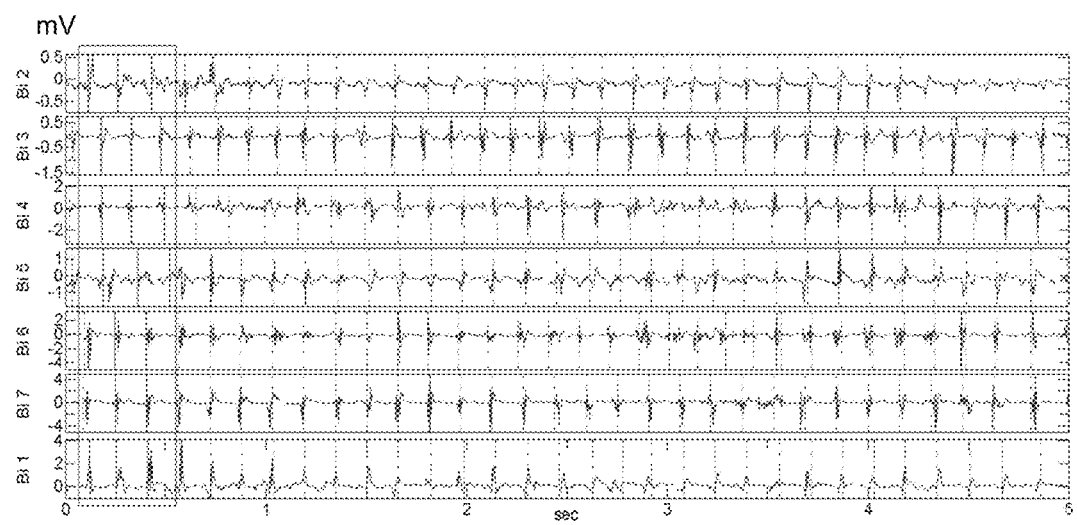
FIG. 17B shows an example of bipolar EGMs obtained over a 5 second duration from the circular catheter location in FIG. 17A.

A similar WC pattern in patient #24 in the study is presented in FIG. 17B. FIG. 17A shows a posterior-anterior view of the left atrium for patient #24 with a circular catheter recording set (1-7 bipoles) located on the posterior wall. The arrows mark the chirality of propagation. FIG. 17B shows bipolar (1-7) electrograms obtained over a 5-second duration from the circular catheter array at the location shown in FIG. 17A. All 7-bipoles had a stable periodicity CL of 158 ms. Periodic activations at each bipole are marked by broken vertical lines. The activation organizes itself to a wave curvature pattern between 0 and 0.6 seconds of the recording (see the boxed area). As there is an activation time difference of >50 ms between adjacent bipoles 2 and 1 in the clockwise direction, it's likely that activation from bipole 2 was blocked clockwise towards bipole 1, but proceeded in a counterclockwise direction in a winding course to bipole 1. This is evident by sequential activations (marked by vertical lines) along the circular catheter in a counterclockwise direction for 3 cycles covering 73% of the periodicity CL 158 ms in each of the first 3 cycles.

Rotational Activation

Two patients had evidence for a RO pattern of propagation transiently appearing on one of their circular catheter recordings. The details of these locations are presented in Table V. The RO mean CL was 164±7 ms, and lasted for 3.5±0.7 cycles. An average of 95±3% of the periodicity CL was covered over the circular catheter bipoles at these locations. FIGS. 18A-18C and FIGS. 19A-19B illustrate the solitary RO pattern seen in patients #50 and #65, respectively. During 5 seconds of AF at these locations, the activation seems to get organized to a RO pattern for 3 and 4 cycles, respectively, with local bipolar EGMs occupying 93% and 97% of their prevailing CL of 169 ms and 159 ms. In patient #50, the RO activation repeats itself for another 3 cycles.

Figure 18A:
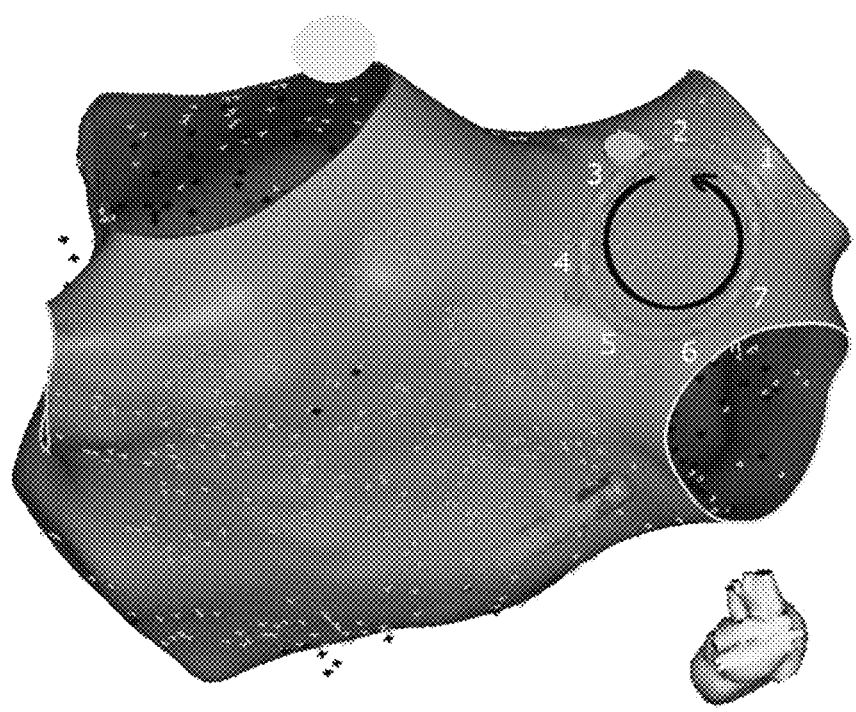
FIG. 18A shows an example of a circular catheter recording set on a posterior wall of a left atrium near the carina of the right PV, with arrows marking the chirality of propagation for patient #50 in the study.
Figure 18B:
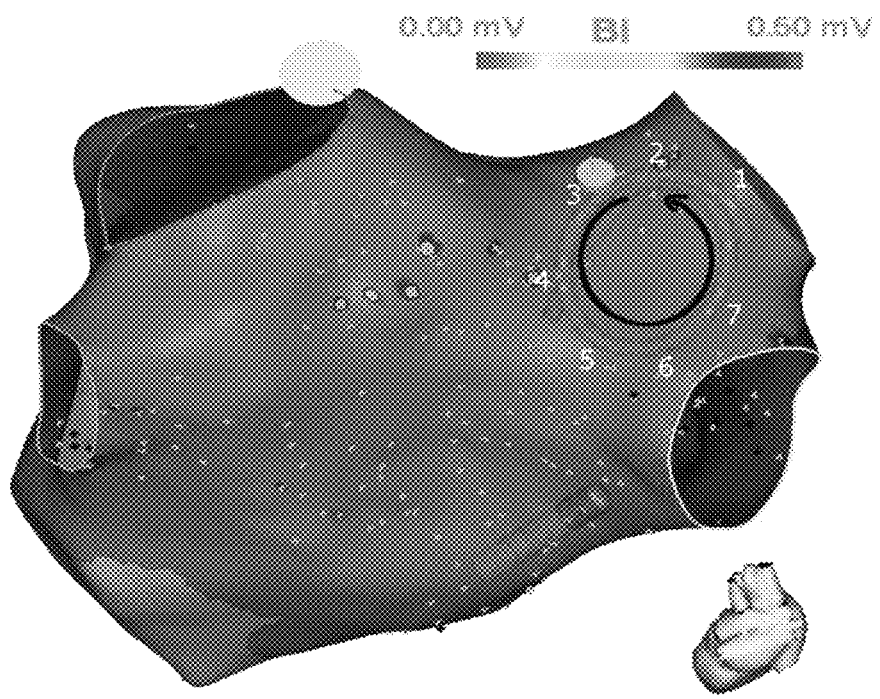
FIG. 18B shows an example of a left atrial voltage map of the same heart and the same view shown in FIG. 18A.
Figure 18C:
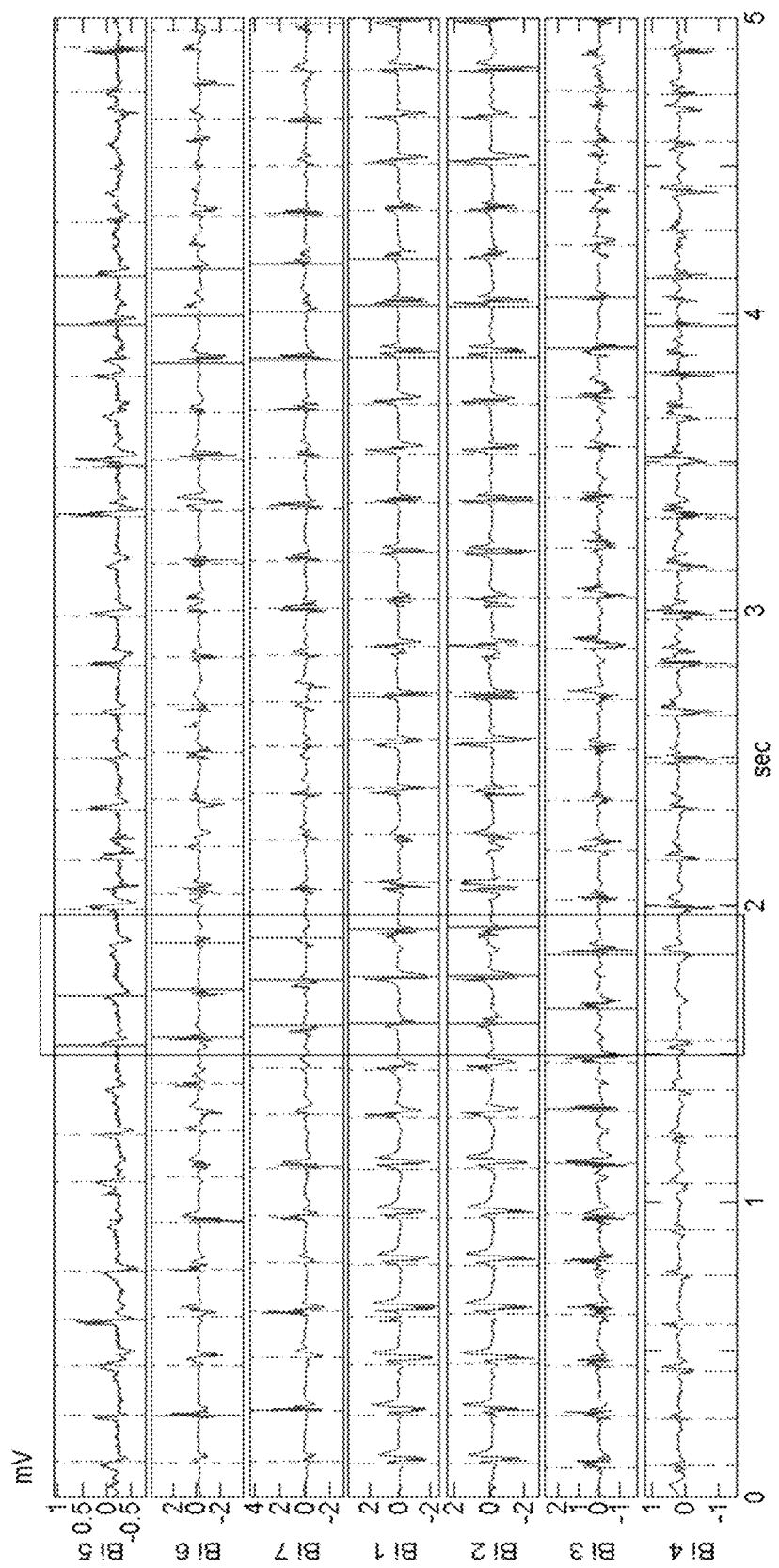
FIG. 18C shows an example of bipolar EGMs obtained over a 5 second duration from the circular catheter location shown in FIG. 18A.

In particular, FIG. 18A shows a posterior-anterior view of left atrium with a circular catheter recording set (1-7 bipoles) located on the posterior wall near the carina of the right PV for patient #50 in the study. FIG. 18B shows a left atrial voltage map based on the same heart and same view as FIG. 18A. There are no significant areas of low voltage on the posterior wall. The arrows in FIGS. 18A-18B mark the chirality of propagation. FIG. 18C shows bipolar (1-7) electrograms obtained over a 5-second duration from the circular catheter location shown in FIG. 18A. Periodic activations at each bipole are marked by broken vertical lines. All 7-bipoles had a stable periodicity CL of 169 ms. The activation organizes itself to a rotation pattern for 4 cycles between 1.5 and 1.9 seconds of the recording and again between 3.8 and 4.15 seconds of recording (see the boxed areas), when activations (marked by vertical lines) travel sequentially in full rotation along the circular catheter covering 93% of the periodicity CL 169 ms.

Figure 19A:
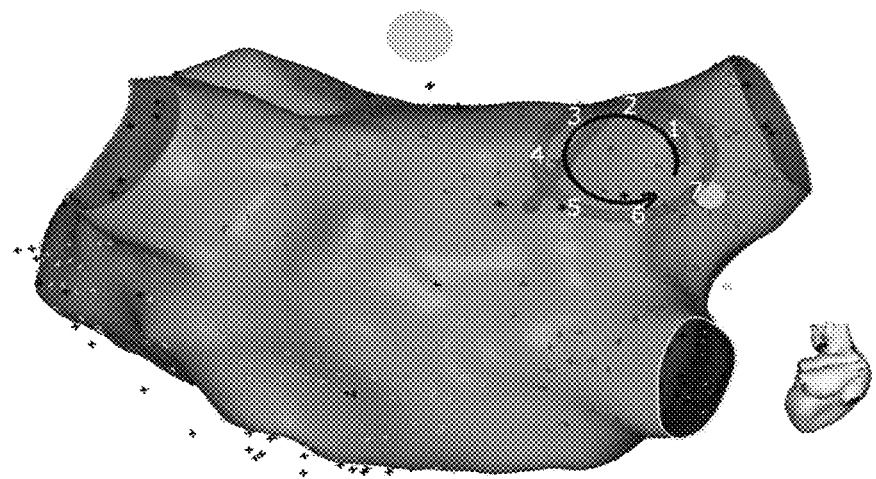
FIG. 19A shows an example of a circular catheter recording set on a posterior wall of a left atrium near the right upper PV, with arrows marking the chirality of propagation for patient #65.
Figure 19B:
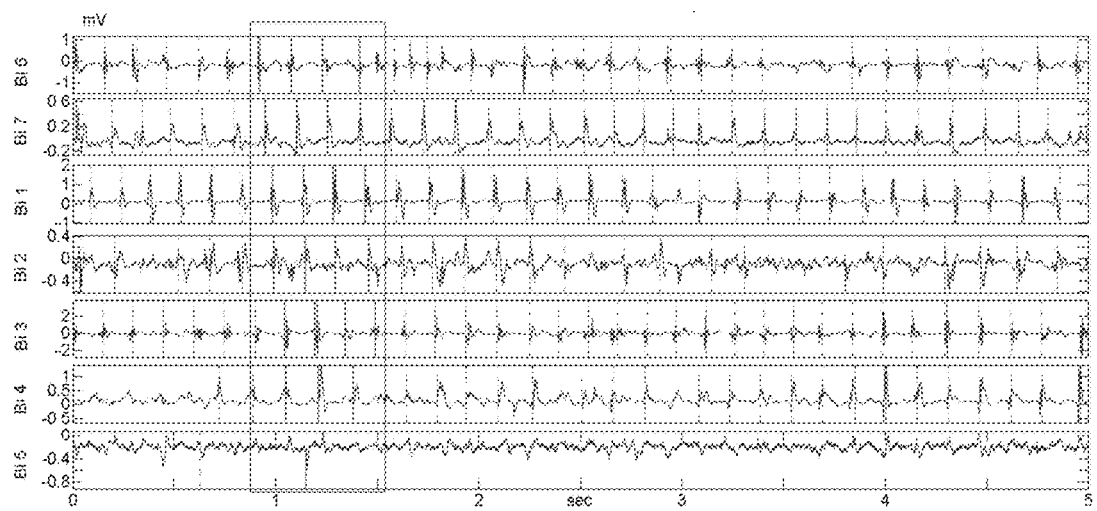
FIG. 19B shows an example of bipolar EGMs obtained over a 5 second duration from the circular catheter location shown in FIG. 19A.

FIG. 19A shows a posterior-anterior view of the left atrium in which a circular catheter recording set (1-7 bipoles) is located on the posterior wall near the right upper PV for patient #65 in the study. The arrows mark the chirality of propagation. FIG. 19B shows bipolar (1-7) electrograms obtained over a 5-second duration from the circular catheter location shown in FIG. 19A. Periodic activations at each bipole are marked by broken vertical red lines. All 7-bipoles had a stable periodicity CL of 159 ms. The activation organizes itself to a rotational pattern for 3 cycles between 0.9 and 1.4 seconds of the recording (see the boxed area), when activations (marked by vertical lines) travel sequentially in full rotation along the circular catheter covering 97% of the periodicity CL 159 ms.

Relation to Bipolar Voltage Map

Only 1 patient (patient #50) had a sinus LA voltage map and an identifiable WC and RO activation. There was virtually no low voltage; thus no particular relationship of WC and RO activations was observed to a low voltage area (see FIGS. 16B and 18B).

TABLE V

Patient characteristics

| Characteristic | Total (N = 70) | No WC/RO activation (N = 62) | WC/RO activation (N = 8)* | p-value |
|---|---|---|---|---|
| Age, years | 61 ± 10 | 61 ± 10 | 56 ± 9 | 0.2 |
| Paroxysmal AF, n (%) | 44 (63) | 40 (64) | 4 (50) | 0.5 |
| Duration of paroxysmal AF, months | 77 ± 65 | 79 ± 66 | 49 ± 14 | 0.037 |
| Persistent AF, n (%) | 26 (37) | 22 (36) | 4 (50) | 0.5 |
| Duration of persistent AF, months | 10 ± 7 | 11 ± 8 | 7 ± 4 | 0.3 |
| Hypertension, n (%) | 30 (43) | 25 (40) | 5 (63) | 0.3 |
| Diabetes mellitus, n (%) | 3 (4) | 3 (5) | 0 (0) | 1.0 |
| Coronary artery disease, n (%) | 1 (1) | 1 (2) | 0 (0) | 1.0 |
| Renal disease, n (%) | 0 (0) | 0 (0) | 0 (0) | 1.0 |
| Obstructive sleep apnea, n (%) | 22 (31) | 19 (31) | 3 (38) | 0.7 |
| Morbid obesity, n (%) | 10 (14) | 8 (13) | 2 (25) | 0.3 |
| Previous stroke, n (%) | 2 (3) | 2 (3) | 0 (0) | 1.0 |
| LA diameter, mm | 41 ± 6 | 41 ± 6 | 40 ± 7 | 0.9 |
| LA volume index, mL/m$^2$ | 42 ± 18 | 43 ± 19 | 33 ± 7 | 0.14 |
| LV ejection fraction, % | 60 ± 7 | 60 ± 7 | 60 ± 2 | 0.8 |
| AADI (propafenone, flecainide), n (%) | 26 (37) | 21 (34) | 5 (63) | 0.14 |
| AADII (sotalol, dofetilide), n (%) | 6 (9) | 6 (10) | 0 (0) | 1.0 |
| AADIII (amiodarone), n (%) | 21 (30) | 18 (29) | 3 (38) | 0.7 |
| ACEI or ARB, n (%) | 4 (6) | 4 (7) | 0 (0) | 1.0 |
| β-Blockers, n (%) | 34 (49) | 28 (45) | 6 (75) | 0.14 |
| Calcium Channel Blocker, n (%) | 13 (19) | 11 (18) | 2 (25) | 0.6 |
| Mean LA appendage cycle length, ms | 189 ± 36 | 193 ± 36 | 162 ± 19 | 0.02 |

*7 patients had a wave curvature pattern, 2 patients had a rotational pattern, 1 patient had both patterns
AAD = antiarrhythmic drug,
ACEI = angiotensin converting enzyme inhibitor,
AF = atrial fibrillation,
ARB = angiotensin receptor blocker,
BMI = body mass index,
LA = left atrium,
LV = left ventricle,
RO = rotational activation,
WC = wave curvature

TABLE VI

Spatial and temporal characteristics of rotational activation and wave curvature

| Propagation pattern type | Patient ID | Location | Number of bipoles on circular catheter with sequential activation | Number of cycles | Cycle length (ms) | Percentage cycle length covered on circular catheter (%) |
|---|---|---|---|---|---|---|
| Wave curvature | 24 | Posterior wall | 6 | 3 | 158 | 73 |
| | 32 | RIPV | 3* | 3 | 186 | 6 |
| | 46 | LAA | 5* | 3 | 180 | 55 |
| | 49 | LSPV | 5* | 2 | 169 | 42 |
| | 50 | LIPV | 6 | 5 | 172 | 50 |
| | 55 | RIPV | 5* | 3 | 172 | 15 |
| | 60 | LAA | 6 | 3 | 154 | 47 |
| Rotational activation | 50 | RSPV | 6 | 3 | 169 | 93 |
| | 65 | RSPV | 6 | 4 | 159 | 97 |

*Complex wave curvature pattern with an additional line of conduction block

Discussion

The major findings of the clinical study are that: (1) sites with periodic activation are common in human AF, and are distributed widely in both PV and extra-PV regions; (2) RO and WC propagation patterns are uncommon and transient; and (3) RO can be distinguished from WC using stringent criteria that consider local conduction block and the proportion of the periodicity CL covered by the propagating rotational wave.

The methodology described herein for the study was found to provide a more robust, objective real-time assessment of rotational activation. The patients in the study had predominant paroxysmal AF with a lesser burden of structural and metabolic factors known to promote atrial myopathy (Miller et al., 2015). Despite a less advanced atrial disease, a small number of WC and RO patterns was observed in the study. In one patient with a sinus voltage map and identifiable WC and RO patterns, a predilection of these patterns to low voltage was not observed. This may suggest that a functional rather than a fixed block may have promoted complete and incomplete rotational activation. The data showing that AF CL was faster by 32 ms in patients with a transient WC or a RO pattern compared to those without also support this proposition.

The study showed that WC and RO activity during human AF may be a conspicuous occurrence. While periodic activation was observed in all patients, it was more ubiquitous in induced rather than spontaneous AF. WC and RO activity was observed infrequently. WC and RO were observed in 9 circular catheter recordings (6 PV, 3 extra-PV) in only 8 of the patients, lasting for 3±0.9 and 3.5±0.7 cycles respectively. These differences may relate to the automated detection of RO in the study using more rigorous criteria than previously reported. However, automated detection of periodic rotational activity does provide a reliable assessment of putative rotors or re-entrant AF drivers.

In an alternative embodiment, real-time mapping of rotational activity may be used to guide catheter ablation therapy in patients with AF, potentially improving procedural outcomes. The various criteria and thresholds provide a robust method that operates more efficiently on a computing device in detecting rotors and distinguishing rotors from other activities, such as wave curvature, such that the rotors detected will likely be clinically relevant as potential targets for AF ablation.

It should be noted that the various rotor detection methods described in accordance with the teachings herein may be used in biomedical signal analysis, such as detecting the periodic activations of a rotor, amidst other periodic activations during AF.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

Andrade J, Khairy P, Dobrev D, and Nattel S, (2014), "Clinical profile and pathophysiology of atrial fibrillation", Circ Res, 114:1453-68.

Benitez D, Gaydecki P A, Zaidi A, and Fitzpatrick A P, (2001), "The use of the Hilbert transform in ECG signal analysis", *Computers in Biology and Medicine*, vol. 31, no. 5, pp. 399-406, Sep.

Coast D A, Stern R M, Cano G G, and Briller S A, (1990), "An approach to cardiac arrhythmia analysis using hidden Markov models", *IEEE Trans Biomed Eng*, vol. 37, no. 9, pp. 826-836, Sep.

Dalvi R, Sugavaneswaran L, Chauhan V S, and Krishnan S, (2013), "Reviving the maximum likelihood method for detecting dominant periodicities from near-periodic signals," presented at the *Digital Signal Processing and Signal Processing Education Meeting (DSP/SPE)*, San Francisco, pp. 256-261.

Dalvi R, Suszko A, and Chauhan V S, (2015), "Graph search based detection of periodic activations in complex periodic signals: Application in atrial fibrillation electrograms", In *Electrical and Computer Engineering (CCECE), 2015 IEEE 28th Canadian Conference on*, pp. 376-381, May.

Dalvi R, Suszko A, Chauhan V S (2016a), "An algorithm for rotor tracking in atrial fibrillation using graph search-based periodic peak detection", Conf Proc IEEE Eng Med Biol Soc 2016, pp. 3473-3477.

Dalvi R, Suszko A, Chauhan V S (2016b), "Identification and annotation of multiple periodic pulse trains using dominant frequency and graph search: Application in atrial fibrillation rotor detection", IEEE Eng. Med Biol. Soc. Aug 2016; pp. 3572-3575.

Ghoraani B, Dalvi R, Gizurarson S, Das M, Ha A, Suszko A, Krishnan S, and Chauhan V S, (2013), "Localized rotational activation in the left atrium during human atrial fibrillation: Relationship to complex fractionated atrial electrograms and low voltage zones", *Heart Rhythm*, 10:1830-38.

Gizurarson S, Dalvi R, Das M, Ha A C T, Suszko A, Chauhan V S, (2016), "Hierarchical Schema for Identifying Focal Electrical Sources During Human Atrial Fibrillation: Implications for Catheter-Based Atrial Substrate Ablation", *JACC: Clinical Electrophysiology*, vol. 2, no. 6, pp. 656-666.

Hadj Slimane Z E, and Nait-Ali A, (2010), "QRS complex detection using Empirical Mode Decomposition", *Digital Signal Processing*, vol. 20, no. 4, pp. 1221-1228, Jul.

Heijman J, Algalarrondo V, Voigt N, Melka J, Wehrens X H, Dobrev D and Nattel S, (2015) "The value of basic research insights into atrial fibrillation mechanisms as a guide to therapeutic innovation: a critical analysis", *Cardiovascular research*, vol. 109, no. 4, pp. 467-479.

Jacobson A L, (2001), "Auto-threshold peak detection in physiological signals" presented at *Engineering in Medicine and Biology Society*, vol. 3, pp. 2194-2195.

Lee G, Kumar S, Teh A, Madry A, Spence S, Larobina M, Goldblatt J, Brown R, Atkinson V, Moten S, Morton J B, Sanders P, Kistler P M, Kalman J M, (2014), "Epicardial wave mapping in human long-lasting persistent atrial fibrillation: transient rotational circuits, complex wavefronts, and disorganized activity", *European Heart Journal*, vol. 35, no. 2, pp. 86-97.

Lee S, Sahadevan J, Khrestian C M, Markowitz A, Waldo A L, (2017), "Characterization of Foci and Breakthrough Sites During Persistent and Long-Standing Persistent Atrial Fibrillation in Patients: Studies Using High-Density (510-512 Electrodes) Biatrial Epicardial Mapping", *Journal of the American Heart Association*, vol. 6, no. 3, pp. e005274.

Lim H S, Yamashita S, Cochet H, Haissaguerre M, (2014), "Delineating atrial scar by electroanatomic voltage mapping versus cardiac magnetic resonance imaging: where to draw the line?", *Journal of Cardiovascular Electrophysiology*, vol. 25, no. 10, pp. 1053-1056.

Lin K P and Chang W H, (1989), "QRS feature extraction using linear prediction", *IEEE Trans Biomed Eng*, vol. 36, no. 10, pp. 1050-1055, Oct.

Mehta S S, Shete D A, Lingayat N S, and Chouhan V S, (2010), "K-means algorithm for the detection and delineation of QRS-complexes in electrocardiogram", *IRBM*, vol. 31, no. 1, pp. 48-54, Feb.

Miller J D, Aronis K N, Chrispin J, Patil K D, Marine J E, Martin S S, Blaha M J, Blumenthal R S, Calkins H (2015), "Obesity, Exercise, Obstructive Sleep Apnea, and Modifiable Atherosclerotic Cardiovascular Disease Risk Factors in Atrial Fibrillation", J Am Coll Cardiol, vol. 66, pp. 2899-2906.

Narayan S M, Krummen D E, and Rappel W J, (2012), "Clinical Mapping Approach To Diagnose Electrical Rotors and Focal Impulse Sources for Human Atrial Fibrillation: Computational Mapping of Rotors and Focal Impulses in Human AF", *Journal of Cardiovascular Electrophysiology*, vol. 23, no. 5, pp. 447-454, May.

Nattel, S, (2002), "New ideas about atrial fibrillation 50 years on", *Nature*, vol. 415, no. 6868, pp. 219-226.

Ng J, and Goldberger J J, (2007), "Understanding and Interpreting Dominant Frequency Analysis of AF Electrograms", *Journal of Cardiovascular Electrophysiology*, vol. 18, no. 6, pp. 680-685, Jun.

Ng J, Sehgal V, Ng J K, Gordon D, and Goldberger J J, (2014), "Iterative method to detect atrial activations and measure cycle length from electrograms during atrial fibrillation", *IEEE Trans Biomed Eng*, vol. 61, no. 2, pp. 273-278, Feb.

Pandit S, and Jalife J, (2013), "Rotors and the dynamics of cardiac fibrillation", Circ Res, 112:849-62.

Panoulas K I, Hadjileontiadis L J, and Panas S M, (2001), "Enhancement of R-wave detection in ECG data analysis using higher-order statistics", presented at *Engineering in Medicine and Biology Society*, vol. 1, pp. 344-347.

Scholkmann F, Boss J, and Wolf M, (2012), "An efficient algorithm for automatic peak detection in noisy periodic and quasi-periodic signals", *Algorithms*, vol. 5, no. 4, pp. 588-603, Nov.

Sethares W A, and Staley T W, (1999), "Periodicity transforms", *Signal Processing, IEEE Transactions on*, vol. 47, no. 11, pp. 2953-2964.

Singh O and Sunkaria R K, (2011), "Article: A robust R-peak detection algorithm using wavelet packets", *International Journal of Computer Applications*, vol. 36, no. 5, pp. 37-43, Dec.

Skanes A C, Mandapati R, Berenfeld O, Davidenko J M, and Jalife J, (1998), "Spatiotemporal Periodicity During Atrial Fibrillation in the Isolated Sheep Heart", *Circulation*, vol. 98, no. 12, pp. 1236-1248, Sep.

Vaquero M, Calvo D, and Jalife J, (2008), "Cardiac fibrillation: from ion channels to rotors in the human heart", *Heart Rhythm*, vol. 5, no. 6, pp. 872-879, Jun.

Vijayakumar R, Vasireddi S K, Cuculich P S, Faddis M N, Rudy Y, (2016), "Methodology considerations in phase mapping of human cardiac arrhythmias", *Circulation: Arrhythmia and Electrophysiology*, vol. 9, no. 11, pp. e004409.

Vivó-Truyols G, Torres-Lapasió J R, van Nederkassel A M, Vander Heyden Y, and Massart D L, (2005), "Automatic program for peak detection and deconvolution of multi-overlapped chromatographic signals part I: peak detection", *J Chromatogr A*, vol. 1096, no. 1-2, pp. 133-145, Nov.

The invention claimed is:

1. A method of detecting a rotor at a location of a heart that experiences cardiac fibrillation, where the method comprises:

obtaining, by a processor, an electrogram (EGM) dataset, where the EGM dataset was recorded using a circular bipolar electrode array positioned at the location of the heart, the circular bipolar electrode array having a plurality of bipolar electrodes for simultaneously recording a plurality of bipolar EGMs for the EGM dataset for a recording duration;

detecting, by the processor, a dominant periodicity Cycle Length (CL) and identifying periodic activations for each bipolar EGM associated with the dominant periodicity CL;

tracking, by the processor, the identified periodic activations across each bipolar EGM to define rotational activations and determining when a path taken by the tracked rotational activations corresponds to a rotational activation pattern of a rotor;

detecting, by the processor, the rotor when a number and completeness of the tracked rotational activations meet predefined rotor criteria including that the tracked rotational activations are greater than at least two complete rotations around the circular bipolar electrode array and the completeness of the tracked rotational activations occurs when a time interval spanned by the rotational activations span across the bipolar EGMs with a time duration where a proportion of the time duration relative to the dominant periodicity CL associated with the rotor is greater than a periodic activation duration threshold.

2. The method of claim 1, wherein the method further comprises, by the processor, displaying an image with information on the location of the detected rotor to guide ablation at the location of the heart when rotor detection occurs at the location.

3. The method of claim 2, wherein after ablation is performed the method comprises, by the processor, repeating the acts of obtaining an EGM dataset; determining the dominant periodicity CL and identifying periodic activations, tracking the periodic activations and detecting the rotor; and repeating ablation when the rotor is still detected.

4. The method of claim 1, wherein the predefined rotor criteria further comprise:

the tracked rotational activations cover a curvature threshold around the circular bipolar electrode array without conduction block.

5. The method of claim 1, wherein the dominant periodicity CL is determined by using a method based on one of spectral analysis, autocorrelation, periodicity transforms, wavelets, Maximum Likelihood (ML), periodic component analysis and Dominant Frequency (DF) analysis.

6. The method of claim 1, wherein periodic activations for a given bipolar EGM are identified, by the processor, by finding peaks in the given bipolar EGM that are associated with the detected dominant periodicity CL by:

removing baseline drift and DC bias in the given bipolar EGM;

finding a set of peaks ($Peak_{EGM}$) that satisfy a minimum voltage gradient threshold and an absolute amplitude threshold;

determining a set of peaks associated with a least cost path on a graph where nodes of the graph of the peaks in Peak$_{EGM}$ and edges of the graph are costs based on a distances between the peaks in Peak$_{EGM}$ relative to the dominant periodicity CL;

selecting different potential starting and ending peaks in Peak$_{EGM}$ until end peaks are found that result in the least cost path; and denoting the set of peaks associated with the least cost path as the actual periodic peaks.

7. The method of claim 6, wherein the method comprises, by the processor, verifying that the actual periodic peaks contain an initial peak and a final peak for a given EGM by:

determining costs for various combinations of actual periodic peaks where each combination includes one of n potential initial peaks and one of m potential final peaks;

locating the combination with the least cost; and setting the peaks in the located combination as the actual periodic peaks.

8. The method of claim 1, wherein tracking the periodic activations across each bipolar EGM to define rotational activations comprises:

grouping the EGMs with a similar dominant periodicity CL into an EGM dataset S1;

verifying that a percentage of EGMs in the EGM dataset S1 is greater than a periodicity similarity threshold; and determining which periodic activations in the EGM dataset S1 are rotor activation candidates based on the presence of temporal progression of the periodic activations across adjacent bipoles of a circular electrode array.

9. The method of claim 1, wherein a current periodic activation EGM$_n$ in an EGM dataset S1 that is unassigned to any candidate rotor is assigned as a rotor activation candidate for a current candidate rotor for a clockwise rotor, when (a) the current periodic activation EGM$_n$ is an earliest periodic activation and the current candidate rotor has no periodic activations assigned to it; or (b) the current periodic activation EGM$_n$ is a nearest periodic activation in a subsequent bipolar EGM and is after, and within, one dominant periodicity CL of a latest periodic activation that was assigned to the current candidate rotor; otherwise, a new candidate rotor is defined when the current periodic activation EGM$_n$ is the nearest annotated periodic activation in a subsequent bipolar EGM that is as yet unassigned to any candidate rotor and is either before the latest periodic activation that was assigned to the current candidate rotor OR after, and more than one dominant periodicity CL away from the latest periodic activation that was assigned to the current candidate rotor and the current periodic activation is assigned to the new candidate rotor.

10. The method of claim 1, wherein a current periodic activation EGM$_n$ in an EGM dataset S1 that is unassigned to any candidate rotor is assigned as a rotor activation candidate for a current candidate rotor that is counter-clockwise rotor when: (a) the current periodic activation EGM$_n$ is an earliest periodic activation and the current candidate rotor has no activations assigned to it; or (b) the current periodic activation EGM$_n$ is a nearest periodic activation in a previous bipolar EGM and is before, and within, one dominant periodicity CL of a latest periodic activation that was assigned to the current candidate rotor; otherwise, a new candidate rotor is defined when the current periodic activation EGM$_n$ is the nearest annotated periodic activation in a subsequent bipolar EGM that is as yet unassigned to any candidate rotor and is either after the latest periodic activation that was assigned to the current candidate rotor OR before, and more than one dominant periodicity CL away from the latest periodic activation that was assigned to the current candidate rotor and the current periodic activation is assigned to the new candidate rotor.

11. The method of claim 1, wherein when the EGM dataset comprises multiple dominant periodicity CL, the method comprises, by the processor, detecting potential rotors associated with the different dominant periodicity CL and selecting the potential rotor having a greatest number of rotations as the detected rotor.

12. The method of claim 11, wherein prior to the act of tracking the identified periodic activations across each bipolar EGM to define rotational activations, the method comprises, by the processor, checking for multiple dominant periodicity CL by:

defining a set of current periodic activations associated with the current dominant periodicity CL;

removing the set of current periodic activations from the bipolar EGMs;

determining if there is an additional dominant periodicity CL; and iterating over the defining, removing and determining acts until all dominant periodicity CL and the associated periodic activations have been found.

13. The method of claim 12, wherein for each set of periodic activations associated with a different dominant periodicity CL, the method further comprises, by the processor, performing the acts of tracking the periodic activations and detecting the rotor to detect the potential rotors associated with the different dominant periodicity CL and determining the number of rotations for each potential rotor.

14. The method of claim 1, wherein when the dominant periodicity CL is larger than a dominant periodicity threshold the location of the heart is considered too slow to function as a rotor of the cardiac fibrillation.

15. The method of claim 1, wherein the method comprises, by the processor, determining when the path taken by the tracked rotational activations corresponds to a wave curvature based on when:

the bipolar EGMs of the tracked rotational activation have a similar periodicity CL and a sequential activation that is greater than a rotor activation candidate threshold; and each tracked rotational activation spans across the bipolar EGMs with a time duration where a proportion of the time duration relative to the dominant periodicity CL associated with the rotor is less than a periodic activation duration threshold.

16. The method of claim 1, wherein the method comprises, by the processor, determining that a given rotational activation includes local conduction block when an activation time difference between two adjacent bipolar EGMs on the circular bipolar electrode array is greater than a time threshold.

17. A non-transitory computer-readable medium storing computer-executable instructions, the instructions when executed cause a processing unit to perform a method of detecting a rotor at a location of a heart that experiences cardiac fibrillation, wherein the method comprises:

obtaining, by the processing unit, an electrogram (EGM) dataset, where the EGM dataset was recorded using a circular bipolar electrode array positioned at the location of the heart, the circular bipolar electrode array having a plurality of bipolar electrodes for simultaneously recording a plurality of bipolar EGMs for the EGM dataset for a recording duration;

detecting, by the processing unit, a dominant periodicity Cycle Length (CL) and identifying periodic activations for each bipolar EGM associated with the dominant periodicity CL;

tracking, by the processing unit, the identified periodic activations across each bipolar EGM to define rotational activations and determining when a path taken by the tracked rotational activations corresponds to a rotational activation pattern of a rotor; and detecting, by the processing unit, the rotor when a number and completeness of the tracked rotational activations meet predefined rotor criteria including that the tracked rotational activations are greater than at least two complete rotations around the circular bipolar electrode array and the completeness of the tracked rotational activations occurs when a time interval spanned by the rotational activations span across the bipolar EGMs with a time duration where a proportion of the time duration relative to the dominant periodicity CL associated with the rotor is greater than a periodic activation duration threshold.

18. The non-transitory computer-readable medium of claim 17, wherein the predefined rotor criteria further comprise:

the tracked rotational activations cover a curvature threshold around the circular bipolar electrode array without conduction block.

19. The non-transitory computer-readable medium of claim 17, wherein tracking the periodic activations across each bipolar EGM to define rotational activations comprises:

grouping the EGMs with a similar dominant periodicity CL into an EGM dataset S1;

verifying that a percentage of EGMs in the EGM dataset S1 is greater than a periodicity similarity threshold; and determining which periodic activations in the EGM dataset S1 are rotor activation candidates based on the presence of temporal progression of the periodic activations across adjacent bipoles of a circular electrode array.

20. The non-transitory computer readable medium of claim 17, wherein when the EGM dataset comprises multiple dominant periodicity CL, the method comprises, by the processing unit, detecting potential rotors associated with the different dominant periodicity CL and selecting the potential rotor having a greatest number of rotations as the detected rotor.

21. The non-transitory computer readable medium of claim 17, wherein the method comprises, by the processing unit, determining that a given rotational activation includes local conduction block when an activation time difference between two adjacent bipolar EGMs on the circular bipolar electrode array is greater than a time threshold.

22. The non-transitory computer readable medium of claim 17, wherein the method comprises, by the processor, displaying an image with information on the location of the detected rotor to guide ablation at the location of the heart when rotor detection occurs at the location.

23. An electronic device detecting a rotor at a location of a heart that experiences cardiac fibrillation, the electrical device comprising:

an input for obtaining an electrogram (EGM) dataset, where the EGM dataset was recorded using a circular bipolar electrode array positioned at the location of the heart, the circular bipolar electrode array having a plurality of bipolar electrodes for simultaneously recording a plurality of bipolar EGMs for the EGM dataset for a recording duration;

a rotor detector coupled to the input to receive the EGM dataset; detect a dominant periodicity Cycle Length (CL) and identify periodic activations for each bipolar EGM associated with the dominant periodicity CL; track the identified periodic activations across each bipolar EGM to define rotational activations and determining when a path taken by the tracked rotational activations corresponds to a rotational activation pattern of a rotor; and detect the rotor when a number and completeness of the tracked rotational activations meet predefined rotor criteria including that the tracked rotational activations are greater than at least two complete rotations around the circular bipolar electrode array and the completeness of the tracked rotational activations occurs when a time interval spanned by the rotational activations span across the bipolar EGMs with a time duration where a proportion of the time duration relative to the dominant periodicity CL associated with the rotor is greater than a periodic activation duration threshold; and an output coupled to the processing unit to output when the rotor is detected and output associated rotor data for a detected rotor.

24. The device of claim 23, wherein the device further comprises:

a processor that is configured to display an image with information on the location of the detected rotor to guide ablation at the location of the heart when rotor detection occurs at the location; and an ablation unit for performing ablation at the location of the heart where the detected rotor is located and after ablation the rotor detector is configured to repeat the acts of obtaining an EGM dataset; detecting a dominant periodicity CL and identifying periodic activations, tracking the periodic activations and detecting the rotor to determine if the ablation was successful.

25. The device of claim 23, wherein the device further comprises a sensor unit that includes the circular bipolar electrode array.

26. The device of claim 23, wherein the predefined rotor criteria further comprises:

the tracked rotational activations cover a curvature threshold around the circular bipolar electrode array without conduction block.

27. The device of claim 23, wherein the rotor detector is configured to track the periodic activations across each bipolar EGM to define rotational activations by:

grouping the EGMs with a similar dominant periodicity CL into an EGM dataset S1;

verifying that a percentage of EGMs in the EGM dataset S1 is greater than a periodicity similarity threshold; and determining which periodic activations in the EGM dataset S1 are rotor activation candidates based on the presence of temporal progression of the periodic activations across adjacent bipoles of a circular electrode array.

28. The device of claim 23, wherein the device further comprises a periodicity filter to separate periodic activations associated with different potential rotors when there are multiple dominant periodicities and select the potential rotor having a greatest number of rotations as the detected rotor.

29. The device of claim 23, wherein the rotor detector is configured to determine that a given rotational activation includes local conduction block when an activation time difference between two adjacent bipolar EGMs on the circular bipolar electrode array is greater than a time threshold.

* * * * *